US007384939B2

(12) United States Patent
Harrington et al.

(10) Patent No.: US 7,384,939 B2
(45) Date of Patent: Jun. 10, 2008

(54) PROCESS FOR PREPARATION OF PYRIDINE DERIVATIVES OF NK-1 RECEPTOR ANTAGONIST

(75) Inventors: Peter J. Harrington, Louisville, CO (US); David A. Johnston, Louisville, CO (US); L. Mark Hodges, Fredrick, CO (US)

(73) Assignee: Roche Colorado Corporation, Boulder, CO (US)

( * ) Notice: Subject to any disclaimer, the term of this patent is extended or adjusted under 35 U.S.C. 154(b) by 140 days.

(21) Appl. No.: 11/175,799

(22) Filed: Jul. 5, 2005

(65) Prior Publication Data

US 2006/0014959 A1      Jan. 19, 2006

Related U.S. Application Data

(60) Provisional application No. 60/585,779, filed on Jul. 6, 2004, provisional application No. 60/655,731, filed on Feb. 23, 2005.

(51) Int. Cl.
| | |
|---|---|
| *A61K 31/54* | (2006.01) |
| *A61K 31/497* | (2006.01) |
| *A61K 31/66* | (2006.01) |
| *C07D 279/10* | (2006.01) |
| *C07D 401/00* | (2006.01) |

(52) U.S. Cl. ............................ 514/227.8; 514/235.5; 514/252.13; 544/58.2; 544/111; 544/361

(58) Field of Classification Search .............. 544/58.2, 544/111, 361; 514/227.8, 235.5, 252.13
See application file for complete search history.

(56) References Cited

U.S. PATENT DOCUMENTS

| 3,853,895 A | 12/1974 | Lamm et al. |
| 4,061,642 A | 12/1977 | Fleckenstein et al. |
| 4,182,887 A | 1/1980 | Roch et al. |
| 2005/0014792 A1 | 1/2005 | Goehring et al. |

FOREIGN PATENT DOCUMENTS

| DE | 10008042 A1 | 8/2000 |
| EP | 1103545 B1 | 5/2003 |
| EP | 1103546 B1 | 10/2003 |
| WO | 02/06236 A1 | 1/2002 |
| WO | 02/08232 A1 | 1/2002 |
| WO | 02/16324 A1 | 2/2002 |
| WO | 02/47663 A1 | 6/2002 |
| WO | 02/079134 A1 | 10/2002 |
| WO | 02/085458 A3 | 10/2002 |
| WO | 03/006016 A2 | 1/2003 |
| WO | 03/011860 A2 | 2/2003 |
| WO | 03/064685 A3 | 8/2003 |
| WO | 04/067007 A1 | 8/2004 |
| WO | 06/002860 A1 | 1/2006 |
| WO | 06/099968 A1 | 9/2006 |

OTHER PUBLICATIONS

Hcaplus 74:53461.*
Harrington, Peter J. et al., "Research and Development of an Efficient Process for the Construction of the 2,4,5-Substituted Pyridines of NK-1 Receptor Antagonists", Organic process Research & Development, 2006:10, pp. 1157-1166.
Hoffmann-Emery et al., "Efficient Synthesis of Novel NK1 Receptor Antagonists: Selective 1,4-Addition of Gridnard Reagents to 6-Chloronicotinic Acid Derivatives", Journal of Organic Chemistry, 2006, vol. 71, No. 5, pp. 2000-2008.
Hoffmann, Torsten et al., "Design and Synthesis of a Novel, Achiral Class of Highly Potent and Selective, Orally Active Neurokinin-1 Receptor Antagonists", Bioorganic & Medicinal Chemistry Letters 16 (2006), pp. 1362-1365.
Humpries, Mark J., et al., "A Fresh AIR Synthesis", Synthesis 1999, No. 6, pp. 985-992.
Katritzky, Alan R., et al., "Preparation of Tetrahydroindolizines from Pyridinium and Isoquinolinium Ylides", J.C.S. Perkin I, 1981, pp. 1180-1185.
Litvinov, V.P., et al., "Pyridinium Ylides in Organic Synthesis. Part 4. Pyridinium Ylides in Nucleophilic Addition-Elimination (Adn-e) Reactions", Russian Journal of Organic Chemistry, vol. 33, No. 7, 1997, pp. 903-940. Translated from Zhurnal Organicheskoi Khimii. vol. 33, No. 7, 1997, pp. 975-1014. Original Russian Text Copyright 1997 by Litvinov, Shessopalov.
Merchant, Kevin J., "Potassium Trimethylsilanolate Mediated Hydrolysis of Nitriles to Primary Amides", Tetrahedron Letters 41 (2000), pp. 3747-3749.
Miyamoto, Teruyuki et al., "Synthesis and Reactions of 7-Substituted 1-Cyclopropyl-6-fluoro-1,4-dihydro-4-oxo-1,8-naphthyridine-3-carboxylic Acids as an Antibacterial Agent [1]", Journal of Heterocyclic Chemistry, vol. 24, Sep.-Oct. 1987, pp. 1333-1339.
Salem, Mounir A. I., et al., "Synthesis of Bactericides Via Carbon Nucleophilic Addition on 1,3-Diarylprop-2-enoned as Michael Acceptors", Heterocycles, vol. 53, No. 5, 2000, pp. 1129-1143.

(Continued)

*Primary Examiner*—Janet L. Andres
*Assistant Examiner*—Binta Robinson
(74) *Attorney, Agent, or Firm*—Faegre & Benson LLP

(57) ABSTRACT

The present invention provides a process for preparing a pyridine compound of the formula:

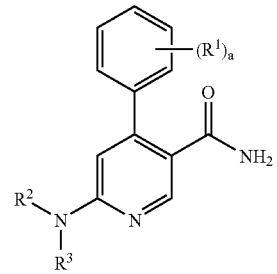

wherein $R^1$, $R^2$, $R^3$ and a are those defined herein.

32 Claims, No Drawings

OTHER PUBLICATIONS

Shestopalov, Yu et al., "Stereochemistry of the Reaction of Pyridinium Ylides With alpha, beta-unsaturated Nitriles", T. G. Shevchenko State Pedagogical Institute, Lugansk 348011. N.D. Zelinskii Institute of Organic Chemistry, Academy of Sciences of the USSR, Moscow 117913. Translated from Khimiya Geterotsiklicheskikh Soedinenii, No. 3, pp. 363-369, Mar. 1990. Original article submitted Jul. 25, 1988, revision submitted Jan. 18, 1989.

Shestopalov, A.M., et al., "Stereoselective Synthesis of trans-4,5-Substituted 1,4,5,6-tetrahydropyridine-2-(olates) thiolates", Synthesis, May 1991, pp. 402-404.

Stout, Steven C., "Neurokinin1 Receptor Antagonists as Potential Antideppressants", Annu. Rev. Pharmacol. Toxicol. 2001.41:877-906.

* cited by examiner

PROCESS FOR PREPARATION OF PYRIDINE DERIVATIVES OF NK-1 RECEPTOR ANTAGONIST

CROSS-REFERENCE TO RELATED APPLICATIONS

This application claims the priority benefit of U.S. Provisional Application Nos. 60/585,779, filed Jul. 6, 2004, and 60/655,731, filed Feb. 23, 2005, which are incorporated herein by reference in their entirety.

FIELD OF THE INVENTION

The present invention is directed to pharmaceutical process chemistry, particularly a production process for the preparation of pyridine derivatives.

BACKGROUND OF THE INVENTION

The tachykinin neuropeptide substance P is a naturally occurring undecapeptide that stimulates contractile action on extravascular smooth muscle tissue upon binding with the receptor Neurokinin 1 (NK-1). NK-1 receptors inhibit the central nervous system (CNS) and peripheral tissues of humans. The interactions of substance P and NK-1 are frequently associated with inflammatory conditions, such as migraine, rheumatoid arthritis, asthma and inflammatory bowel disease. In addition, the modulation of Parkinson's disease and other disorders of the CNS and mediation of the emetic reflex are attributed to substance P/NK-1 contact.

NK-1 antagonists inhibit the interaction of substance P and NK-1 receptor site. These antagonists have previously been utilized for treatment of pain, headache, migraine, Alzheimer's disease, multiple sclerosis, attenuation of morphine withdrawal, cardiovascular changes, edema, chronic inflammatory disease, asthma/bronchial hyperactivity, allergic rhinitis, inflammatory diseases of the gut, ocular injuries and ocular inflammatory disease. Such compounds are also believed to be useful in the treatment of various psychological disorders, including disorders of the CNS, as well as treatment of motion sickness, inducement of vomiting and reduction of cisplatin-induced emesis. See Stout, S. C., et al., *Annu. Rev. Pharmacol. Toxicol.* (2001) 41, 877, which is incorporated herein by reference in its entirety.

The conventional processes for synthesis of the pyridine ring structure of Roche's NK-1 antagonists require functionalization of a 2,5-disubstituted pyridine. One of the current methods for producing N-[6-(4-morpholinyl)-3-pyridinyl]pivalamide from 2-chloro-5-nitropyridine involves displacement of the chloro group with morpholine, reduction of the nitro group and acylation of the resulting amine by a pivaloyl group, such as pivaloyl chloride or pivaloyl anhydride. Regioselective lithiation of N-[6-(4-morpholinyl)-3-pyridinyl]pivalamide followed by reaction with an iodide source (such as iodine) then provides a 4-iodopyridine compound, which is used in a Suzuki coupling with an arylboronic acid. The coupled product is then hydrolyzed to remove the pivaloyl group. N-Methylation and acylation of the resulting aminopyridine compound then provides a 2,4,5-tri-substituted pyridine compound. See European Patent No. 1,103,545 (Ballard, T. M. et al.), which is incorporated herein by reference in its entirety. The cost of this process is relatively high due to the need for lithiation. In addition, this process requires production of nitropyridine, which presents a safety hazard.

Another process for producing pyridine ring system based NK-1 receptor agonist utilizes Hoffman rearrangement reaction of a nicotinamide compound. In this process, microbial oxidation of nicotinic acid is used to produce 6-hydroxynicotinic acid, which is then converted to 6-chloronicotinic acid. The carboxylic acid group is then converted to a tert-butylamide group by converting the carboxylic acid to an acid chloride and reacting the acid chloride with tert-butylamine. The resulting pyridine compound is then reacted with o-tolylmagnesium chloride, followed by an oxidation of the resulting product to produce a 4-(o-tolyl) substituted pyridine compound. The overall yield of this process is often low, and requires an excess amount of o-tolylmagnesium chloride. In addition, an oxidation reaction is required to regenerate the pyridine ring system. Removal of the tert-butyl group followed by Hoffman rearrangement of the amide group results in a formation of an isocyanate which is then trapped with methanol to yield a carbamate. The overall production cost of this process is high due to use of expensive starting materials. And furthermore, the overall production efficiency of this process is low due to variability in the success of the Grignard reaction.

Additional known methods for producing pyridine compounds include the Hantzsch, Kröhnke and Guareschi-Thorpe syntheses. Preparation of pyridine compounds via the Guareschi-Thorpe synthesis uses cyanoacetamide and an arylacetate (e.g., ethyl benzoylacetate) as starting materials. See U.S. Pat. No. 4,182,887, issued to Roch, J. et al., which is incorporated herein by reference in its entirety. This process results in a low yield (42%) of 2,6-dihydroxy-3-cyano-4-phenylpyridine with bezoylacetate and still a lower yield when an aryl group is ortho-substituted.

Trans-4-Aryl-3-cyano-6-ox-5-pyridino-1,4,5,6-tetrahydropyridin-2-olates can also be prepared by reaction of a pyridinium salt, an aromatic aldehyde and ethyl cyanoacetate in the presence of a base. See, e.g., Shestopalov, A. M., et al. *Synthesis* (1991) 402; Shestopalov, A. M., et al. *Khim. Geterotsikl. Soedin.* (1990) 363; and Litvinov, V. P., Shestopalov, A. M. *Zh. Org. Khim.* (1997) 33, 975, which are incorporated herein by reference in their entireties.

Another suitable starting material for the production of the NK-1 antagonist pyridine derivative is an amide of the formula:

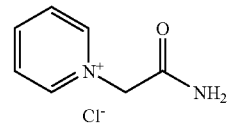

This acetamide compound can be obtained in good yield by the reaction of 2-chloroacetamide with pyridine. See Katritzky, A. F., et al. *J. C. S. Perkins I* (1981) 1180–1185.

Regioselective displacement of chloride from the 2,6-dichloro-3-cyanopyridine by an amine and the conversion of the nicotinonitrile to a nicotinamide are well known to one skilled in the art. In general, unhindered primary amines attack at the 2-position, while hindered primary and secondary amines attack at the 6-position. See U.S. Pat. No. 4,061,642, issued to Fleckenstein, E et al., and U.S. Pat. No. 3,853,895, issued to Lamm, G. and Dehnert, J., which are incorporated herein by reference in their entireties. Hydrolysis of a nicotinonitrile to a nicotinamide compound can be achieved using a variety of reagents, including sulfuric acid, aqueous hydroxide, basic hydrogen peroxide or potassium trimethylsilanolate. See, e.g., Miyamoto, T., et al. *Het. Chem.* (1987) 24, 1333; Salem, M., et al. *Heterocycles* (2000) 53, 1129; Humphries, M., Ramsden, C., *Sythesis* (1999) 985; Merchant, K., *Tet. Lett.* (2000) 41, 3747, all of which are incorporated herein by reference in their entireties.

While methods are available for the production of pyridine derivatives, there exists a need for a pyridine compound production process that utilizes low cost starting materials. There is also a need for a process that avoids the shortcoming of the Grignard reaction's variability.

SUMMARY OF THE INVENTION

The present invention provides a process for preparing a carboxamide pyridine compound of the formula:

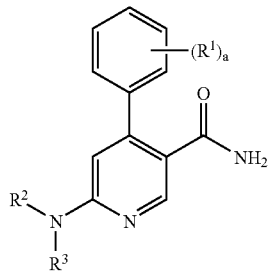

I where
  each $R^1$ is independently lower alkyl, lower alkoxy, halogen, cyano or alkylamino;
  a is an integer from 0 to 2;
  $R^2$ is hydrogen, $C_{3-6}$ cycloalkyl, aralkyl, lower alkyl, hydroxylalkyl, —S(O)$_2$-lower alkyl,
    —S(O)$_2$—Ar$^1$, (optionally substituted N-heterocyclyl) alkyl, —C(=O)R$^3$, where
    Ar$^1$ is aryl, preferably phenyl;
  $R^3$ is hydrogen, $C_{3-6}$ cycloalkyl, aralkyl or lower alkyl;
  or $R^2$ and $R^3$ together with the nitrogen atom to which they are attached to form optionally substituted N-heterocyclyl;
  or $R^2$ and $R^3$ together form =C(R$^5$)—R$^6$—NR$^7$R$^8$;
    where
      $R^5$ is lower alkyl, or preferably hydrogen;
      $R^6$ is alkylene or preferably a bond (i.e., absent); and
      each of $R^7$ and $R^8$ is independently hydrogen, $C_{3-6}$ cycloalkyl, aralkyl, or lower alkyl.

The carboxamide pyridine Compounds of Formula I are useful intermediates in the preparation of Neurokinin-1 receptor antagonists.

The present invention also provides processes for preparing a variety of intermediates that can be used to synthesize carboxamide pyridine compounds of Formula I.

In one embodiment, methods of the present invention include reacting a pyridinium salt of the formula:

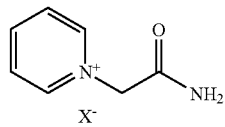

VI with an α-cyano-β-aryl acrylate compound of the formula:

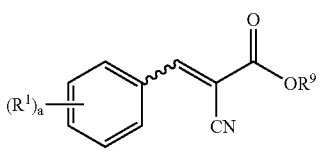

IV to produce a pyridinium zwitter ionic compound of the formula:

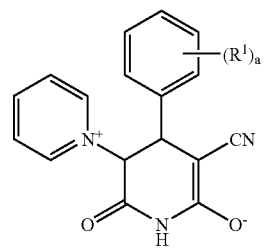

VII where X is halide, $R^9$ is lower alkyl, a, and $R^1$ are those defined herein.

The α-cyano-β-aryl acrylate compound of Formula IV can be prepared by reacting a benzaldehyde compound of the formula:

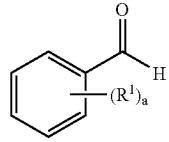

III with an α-cyanoester compound of the formula:

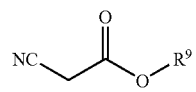

XI in the presence of a base, where a, $R^1$, $R^9$ are those defined herein.

The α-cyano-β-aryl acrylate compound of Formula IV can be prepared separately (i.e., in a separate step or process) or it can be prepared in situ.

In another aspect of the present invention, the pyridinium zwitter ionic compound of Formula VII is treated with a reagent selected from POCl$_3$, PBr$_3$, and (F$_3$CSO$_2$)$_2$O to form a cyanopyridine compound of formula:

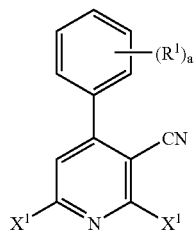

VIII where X$^1$ is halogen or trifluoromethanesufonate; and R$^1$ and a are those defined herein. Regioselective amination of the cyanopyridine compound of formula VIII with an amine compound of the formula HNR$^2$R$^3$ then provides a tetra-substituted pyridine compound of the formula:

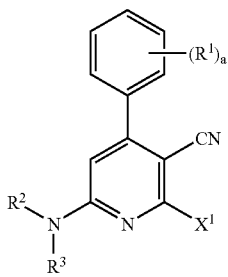

IX where a, R$^1$, R$^2$, R$^3$ and X$^1$ are those defined herein.

Methods of the present invention can also include hydrogenating the tetra-substituted pyridine compound of Formula IX in the presence of a hydrogenation catalyst to form a tri-substituted pyridine compound of the formula:

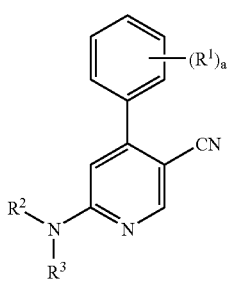

X where a, R$^1$, R$^2$, and R$^3$ are those defined herein.

In addition, methods of the present invention can further include hydrolyzing the tri-substituted pyridine compound of Formula X to form the carboxamide compound of Formula I.

DETAILED DESCRIPTION OF THE INVENTION

Definitions

The following definitions apply generally to terms used in this description regardless of whether the term appears alone or in conjunction.

"Acyl activating group" refers to a group which facilitates transfer of an acyl group to an amine or a hydroxy functional group. Exemplary acyl activation groups include, but are not limited to, halides (such as chlorides as in acid chlorides), anhydrides, and thioesters. Other acyl activating groups are well known to one skilled in the art and can be found, among others, in Smith and March, *Advanced Organic Chemistry*, 5th ed., John Wiley & Sons, New York, N.Y., 2001 and Harrison and Harrison et al., *Compendium of Synthetic Organic Methods*, Vols. 1–8 (John Wiley and Sons, 1971–1996), all of which are incorporated herein by reference in their entirety.

"Alkylene" means a saturated linear saturated divalent hydrocarbon moiety of one to twelve carbon atoms or a branched saturated divalent hydrocarbon moiety of three to twelve carbon atoms. Exemplary alkylene groups include, but are not limited to, methylene, ethylene, propylene, butylene, pentylene, and the like.

"Aralkyl" means a moiety of the formula —R$^b$R$^c$ where R$^b$ is an alkylene group and R$^c$ is an aryl group. Exemplary aralkyl groups include, but are not limited to, benzyl, phenylethyl, 3-(3-chlorophenyl)-2-methylpentyl, and the like, with benzyl being the preferred aralkyl group.

The term "lower alkyl" means a straight- or branched-chain alkyl group containing from 1–7 carbon atoms, for example, methyl, ethyl, propyl, isopropyl, n-butyl, i-butyl, t-butyl, and the like. Preferred lower alkyl groups are groups with 1–4 carbon atoms.

The term "lower alkoxy" means a group wherein the alkyl residues are as defined above, and which is attached via oxygen atom.

The terms "halogen" and "halide" are used interchangeably herein and means chlorine, iodine, fluorine or bromine.

The term "cycloalkyl" means a saturated carbocyclic group, containing 3–6 carbon atoms.

"Heterocyclyl" means an aromatic or non-aromatic cyclic moiety having one or more ring heteroatoms, preferably one or two, each of which is independently selected from N, O, S(O)$_m$ (where m is 0, 1 or 2) with the remaining ring atoms being C. Exemplary heterocyclyl groups include, but are not limited to, morpholinyl, thiomorpholinyl, 1,1-dioxo-1λ$^6$-thiomorpholinyl, piperazinyl and the like.

"Heterocyclylalkyl" means a moiety of the formula —R$^d$—R$^e$, where R$^d$ is alkylene and R$^e$ is heterocyclyl as defined herein.

The term "N-heterocyclyl" refers to a heterocyclyl moiety comprising a nitrogen ring atom and the remaining ring atoms being carbon atoms, with the understanding that the point of attachment of N-heterocyclyl moiety is through the ring nitrogen atom. N-Heterocyclyl may optionally be substituted with hydroxy, lower alkyl, —R$^a$—COO—R$^b$ (where R$^a$ is a bond or alkylene, and R$^b$ is lower alkyl), —N(R$^c$)C (=O)-lower alkyl (where R$^c$ is hydrogen, C$_{3-6}$ cycloalkyl, aralkyl or lower alkyl), hydroxylalkyl, cyano, —R$^e$—O—R$^f$ (where R$^e$ is alkylene and R$^f$ is hydroxylalkyl), —CHO, 5- and 6-membered heterocyclyl, or 5- or 6-membered heterocyclylalkyl.

The term "5 or 6 membered heterocyclyl" refers to a heterocyclyl moiety having 5 or 6 ring atoms. Exemplary 5 or 6 membered heterocyclyl moieties include pyridinyl, pyridimidinyl, oxadiazolyl, triazolyl, tetrazolyl, thiazolyl, thienyl, furyl, pyranyl, pyrrolyl, imidazolyl, pyrazolyl, isothiazolyl, piperazinyl, or piperidyl.

"Hydroxylalkyl" refers to an alkyl, preferably lower alkyl, moiety as defined herein that is substituted with one or more hydroxyl group, provided that no two carbon atom contains more than one hydroxyl group. Preferably, a hydroxyalkyl moiety is of the formula —$R^g$—OH (where $R^g$ is alkylene, i.e., where the hydroxyl group is attached to the terminal carbon atom).

Process for Preparing Compounds of Formula I

One aspect of the present invention provides a process for preparing an amino-substituted cyanopyridine compound of the formula:

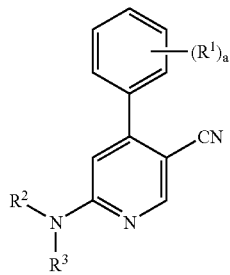

X by reacting a pyridinium salt of the formula:

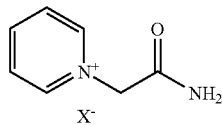

VI with an (α-cyano-β-aryl acrylate compound of the formula:

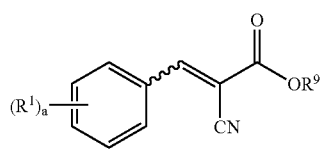

IV to produce a pyridinium zwitter ionic compound of the formula:

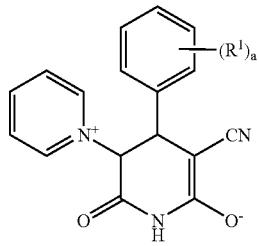

VII where
  each $R^1$ is independently lower alkyl, lower alkoxy, halogen, cyano or alkylamino;
  a is an integer from 0 to 2;
  $R^2$ is hydrogen, $C_{3-6}$ cycloalkyl, aralkyl, lower alkyl, hydroxylalkyl, —$S(O)_2$-lower alkyl,
    —$S(O)_2$—$Ar^1$, (optionally substituted N-heterocyclyl) alkyl, —C(=O)$R^3$, where
    $Ar^1$ is aryl, preferably phenyl;
  $R^3$ is hydrogen, $C_{3-6}$ cycloalkyl, aralkyl or lower alkyl;
  or $R^2$ and $R^3$ together with the nitrogen atom to which they are attached to form optionally substituted N-heterocyclyl;
  or $R^2$ and $R^3$ together form =C($R^5$)—$R^6$—$NR^7R^8$;
    where
    $R^5$ is lower alkyl, or preferably hydrogen;
    $R^6$ is alkylene or preferably a bond (i.e., absent); and
    each of $R^7$ and $R^8$ is independently hydrogen, $C_{3-6}$ cycloalkyl, aralkyl, or lower alkyl;
  $R^9$ is lower alkyl; and
  X is halide.

The pyridinium zwitter ionic compound of Formula VII is then reacted with a reagent selected from POCl$_3$, PBr$_3$, (F$_3$CSO$_2$)$_2$O, and other similar reagents known to one skilled in the art, to form a cyanopyridine compound of the formula:

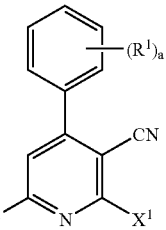

VIII and the cyanopyridine compound of formula VIII is reacted with an amine compound of the formula HNR$^2$R$^3$ to form a tetra-substituted pyridine compound of the formula:

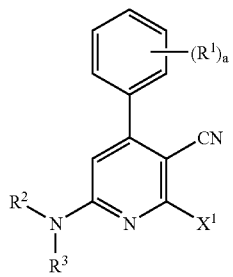

which is then hydrogenated in the presence of a hydrogenation catalyst to form the amino-substituted cyanopyridine compound of the Formula X, where a, $R^1$, $R^2$, and $R^3$ are those defined herein, and each $X^1$ is independently halide or trifluoromethanesufonate. Preferably, both $X^1$ are of the same moiety.

The (α-cyano-β-aryl acrylate compound of Formula IV can be prepared by reacting a benzaldehyde compound of the formula:

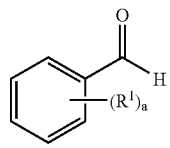

with an α-cyanoester compound of the formula:

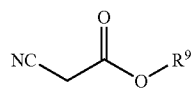

in the presence of a base, wherein a, $R^1$, and $R^9$ are those defined herein. Moreover, the α-cyano-β-aryl acrylate compound of Formula IV can be prepared and separated prior to use or it can be is prepared and used in situ.

Hydrolyzing the amino-substituted cyanopyridine compound of the Formula X provides a carboxamide pyridine compound of the formula:

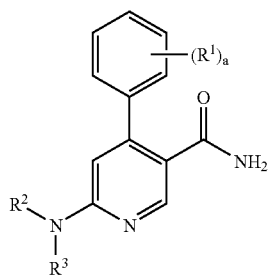

where a, $R^1$, $R^2$, and $R^3$ are those defined herein. As stated above, the carboxamide pyridine compound of Formula I is useful as a valuable intermediate in the synthesis of Neurokinin-1 receptor antagonists, such as those disclosed in PCT Publication No. WO 02/085458, which is incorporated herein by reference in its entirety.

In particular, the carboxamide pyridine compound of Formula I is useful as an intermediate in the synthesis of an aminopyridine compound of the formula:

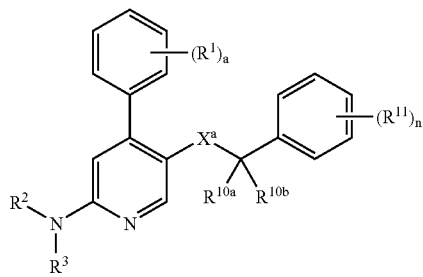

where
a, $R^1$, $R^2$, and $R^3$ are those defined herein,
each of $R^{10a}$ and $R^{10b}$ is independently hydrogen or lower alkyl, or $R^{10a}$ and $R^{10b}$ together with the carbon atom to which they are attached to form a cycloalkyl group;
each $R^{11}$ is independently halide, trifluoromethyl, lower alkoxy, or cyano, or two $R^{11}$ moieties together form —$CR^w$=$CR^x$—$CR^y$=$CR^z$—, where each of $R^w$, $R^x$, $R^y$, and $R^z$ is independently selected from the group consisting of hydrogen, lower alkyl or lower alkoxy, provided that at least two of $R^w$, $R^x$, $R^y$, and $R^z$ are hydrogen;
n is an integer from 0 to 5; and
$X^a$ is —C(=O)N($R^{14}$)—, —$R^{16}$—O—, —$R^{16}$—N($R^{14}$)—, —N($R^{14}$)C(=O)—, or —N($R^{14}$)—$R^{16}$—,
where
$R^{14}$ is hydrogen, $C_{3-6}$ cycloalkyl, aralkyl or lower alkyl; and
$R^{16}$ is alkylene, preferably methylene or ethylene.

Preparation of the aminopyridine compounds of Formula II, which are known Neurokinin-1 receptor antagonist, can be achieved by one of several processes illustrated below. It should be appreciated that the preparation of the aminopyridine compounds of Formula II from the carboxamide pyridine compound of Formula I discussed below are only illustrative and the scope of the present invention is not limited to such processes.

In one particular embodiment, the aminopyridine compounds of Formula II can be prepared from the carboxamide pyridine compound of Formula I by:

(a) reacting the carboxamide pyridine compound of Formula I with an oxidizing agent in the presence of an alcohol of the formula $R^{13}$—OH to produce a carbamate pyridine compound of the formula:

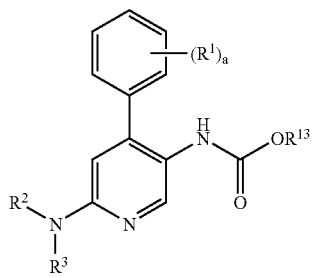
XII (b) reducing the carbamate pyridine compound of Formula XII with a reducing agent to produce a diaminopyridine compound of the formula:

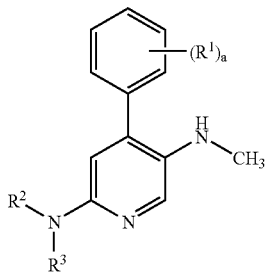
XIII (c) reacting the diaminopyridine compound of Formula XIII with a carbonyl compound of the formula:

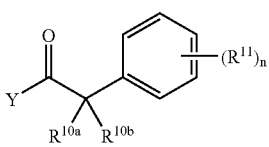
XIV to form the aminopyridine compound of Formula II, where $X^a$ is —N(CH$_3$)C(=O)—; and (d) optionally reacting the aminopyridine compound of Formula II, where $X^a$ is —N(CH$_3$)C(=O)—, with a second reducing agent to produce the aminopyridine compound of Formula II (where $X^a$ is —N(CH$_3$)—CH$_2$—), where
  a, n, R$^1$, R$^2$, R$^3$, R$^{10a}$, R$^{10b}$, and R$^{11}$ are those defined herein;
  R$^{13}$ is lower alkyl; and
  Y is alkoxide or an acyl activating group.

It should be appreciated that a compound of Formula I can be reacted with an oxidizing agent and hydrolyzed with water rather than R$^{13}$—OH to produce a diaminopyridine compound of the formula:

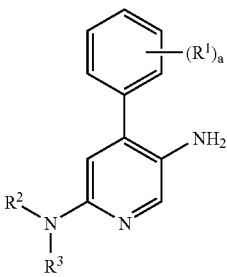
XIIIA

This diaminopyridine of Formula XIIIA can then be further derivatized using similar processes and/or reactions as those described in reference to compounds of Formula XIII to produce corresponding compounds of Formula II.

Some aminopyridine compounds of formulas II can be prepared from the diaminopyridine compound of Formula XIIIA by alkylating with an aralkyl compound of the formula:

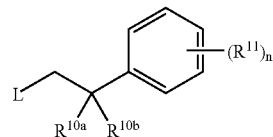
XVIA to produce the aminopyridine compounds of formulas II where $X^a$ is —N(H)—CH$_2$—, L is a leaving group, and R$^{10a}$, R$^{10b}$, R$^{11}$, and n are those defined herein.

In another embodiment, the aminopyridine compounds of Formula II can be prepared from the carboxamide pyridine compound of Formula I by:

(a) contacting the carboxamide pyridine compound of Formula I with a reducing agent to produce an alkylamino-substituted pyridine compound of the formula:

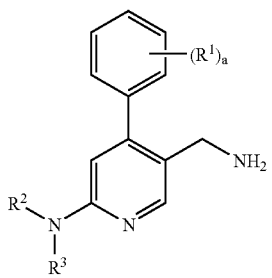
XV and (b) reacting the alkylamino-substituted pyridine compound of Formula XV with an aralkyl compound of the formula:

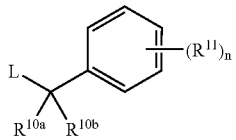

XVI to produce the aminopyridine compound of Formula II, where a, n, $R^1$, $R^2$, $R^3$, $R^{10a}$, $R^{10b}$, and $R^{11}$ are those defined herein;

L is a leaving group; and $X^a$ is —$CH_2N(H)$—.

It should be appreciated that when $X^a$ is —$CH_2N(H)$— or —$N(H)$—$CH_2$— in compounds of Formula II, the amino group of $X^a$ can be further alkylated to produce a substituted $X^a$ group, where $X^a$ is —$CH_2N(R^{14a})$— or —$N(R^{14a})$—$CH_2$—, where $R^{14a}$ is $C_{3-6}$ cycloalkyl, aralkyl or lower alkyl. Typically this alkylation can be achieved with a corresponding $R^{14a}$—$X^b$, where $R^{14a}$ those defined above and $X^b$ is a leaving group. Such alkylation reactions are well known to one of ordinary skill in the art. See, for example, Smith and March, *Advanced Organic Chemistry*, 5th ed. and Harrison and Harrison et al., *Compendium of Synthetic Organic Methods*, Vols. 1–8, all of which are incorporated herein.

Alternatively, rather than by an alkylation reaction, a reductive amination reaction can also be used to substitute the amino group with $R^{14a}$ group. Briefly, a reductive amination involves reacting the amino group $X^a$ (where $X^a$ is —$CH_2N(H)$— or —$N(H)$—$CH_2$—) with an $R^{14a}$ group having a carbonyl group (i.e., a corresponding $R^{14a}$ carbonyl compound) in the presence of a reducing agent, such as sodium borohydride or other similar reducing agent. For example, when $R^{14a}$ is an ethyl group, the corresponding $R^{14a}$ carbonyl compound is HC(=O)$CH_3$, when $R^{14a}$ is benzyl group, the corresponding $R^{14a}$ carbonyl compound is HC(=O)Ph, and when $R^{14a}$ is cyclohexane, the corresponding $R^{14a}$ carbonyl compound is cyclohexanone. Thus, the corresponding $R^{14a}$ carbonyl compound refers to a compound having a carbonyl group within the $R^{14a}$ moiety such that the reductive amination provided substitution of $R^{14a}$ group. Reductive amination reaction is also disclosed in Smith and March, *Advanced Organic Chemistry*, 5th ed., and Harrison and Harrison et al., *Compendium of Synthetic Organic Methods*, Vols. 1–8, which have been incorporated by reference above.

Still alternatively, synthesis of compounds where $R^{14a}$ is an aralkyl or a lower alkyl can involve acylation of the $X^a$ moiety (where the initial $X^a$ moiety is —$CH_2N(H)$— or —$N(H)$—$CH_2$—) with a $R^{15}$—C(=O)—$X^c$, where $X^c$ is an acyl activating group such as halide or ester (i.e., —$OR^{16}$, where $R^{16}$ is an alkyl or other hydrocarbon moiety) and reduction with a suitable reducing agent such as $LiAlBH_4$. Other suitable reducing agents are well known to one skilled in the art as disclosed by Smith and March in Advanced Organic Chemistry, 5th ed. and Harrison and Harrison et al., *Compendium of Synthetic Organic Methods*, Vols. 1–8, which have been previous incorporated by reference. Thus, an $R^{14a}$ group is incorporated by using the acylating agent $R^{15}$—C(=O)—$X^c$, where $R^{15}$—$CH_2$— group represents $R^{14a}$ moiety. Accordingly, in these instances, $R^{14a}$ is a methylene homolog of $R^{15}$ moiety.

Yet in another embodiment, some aminopyridine compounds of Formula II can be prepared from the carboxamide pyridine compound of Formula I by reacting the carboxamide pyridine compound of Formula I with an aralkyl compound of the formula:

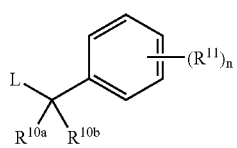

XVI in the presence of a base to produce the aminopyridine compound of Formula II, where n, $R^{10a}$, $R^{10b}$, $R^{11}$, and L are those defined herein.

Other processes for producing aminopyridine compounds of Formula II can be found in PCT Publication Nos: WO 02/085458 and WO 03/011860, and European Patent No. 1 103 545, all of which are incorporated herein by reference in their entirety.

Using processes of the present invention, a wide variety of aminopyridine compounds of Formula II can be prepared including, but not limited to:

N-(3,5-bis-trifluoromethyl-benzyl)-N-methyl-6-[methyl-(2-morpholin-4-yl-ethyl)-amino]-4-o-tolyl-nicotinamide;

N-(3,5-bis-trifluoromethyl-benzyl)-N-methyl-6-morpholin-4-yl-4-o-tolyl-nicotinamide;

N-(3,5-bis-trifluoromethyl-benzyl)-N-methyl-6-thiomorpholin-4-yl-4-o-tolyl-nicotinamide;

N-(3,5-bis-trifluoromethyl-benzyl)-N-methyl-6-(1-oxo-$1\lambda^6$-4-thiomorpholin-4-yl)-4-o-tolyl-nicotinamide;

N-(3,5-bis-trifluoromethyl-benzyl)-6-(1,1-dioxo-$1\lambda^6$-6-thiomorpholin-4-yl)-N-methyl-4-o-tolyl-nicotinamide;

N-(3,5-bis-trifluoromethyl-benzyl)-N-methyl-6-piperazin-1-yl-4-o-tolyl-nicotinamide;

N-(3,5-bis-trifluoromethyl-benzyl)-6-[4-(2-hydroxyethyl)-piperazin-1-yl)]-N-methyl-4-o-tolyl-nicotinamide;

2-(3,5-bis-trifluoromethyl-phenyl)-N-[6-(4-methyl-piperazin-1-yl)-4-o-tolyl-pyridin-3-yl]-N-methyl-isobutyramide;

2-(3,5-bis-trifluoromethyl-phenyl)-N-(6-morpholin-4-yl-4-o-tolyl-pyridin-3-yl)-N-methyl-isobutyramide;

2-(3,5-bis-trifluoromethyl-phenyl)-N-[4-(4-fluoro-2-methyl-phenyl)-6-(4-methyl-piperazin-1-yl)-pyridin-3-yl]-N-methyl-isobutyramide;

2-(3,5-bis-trifluoromethyl-phenyl)-N-[4-(2-chloro-phenyl)pyridin-3-yl]-N-methyl-isobutyramide;

2-(3,5-bis-trifluoromethyl-phenyl)-N-methyl-N-(4-o-tolyl-pyridin-3-yl)-isobutyramide;

2-(3,5-bis-trifluoromethyl-phenyl)-N-methyl-N-[6-(4-pyridin-2-yl-piperazin-1-yl)-4-o-tolyl-pyridin-3-yl)-isobutyramide;

2-(3,5-bis-trifluoromethyl-phenyl)-N-(6-morpholin-4-yl-4-o-tolyl-pyridin-3-yl)-isobutyramide;

2-(3,5-bis-trifluoromethyl-phenyl)-N-[4-(2-chlorophenyl)-6-dimethylamino-pyridin-3-yl]-isobutyramide;

2-(3,5-bis-trifluoromethyl-phenyl)-N-methyl-N-(6-piperazin-1-yl-4-o-tolyl-pyridin-3-yl)-isobutyramide; or 2-(3,5-bis-trifluoromethyl-phenyl)-N-[6-(1,1-dioxo-$1\lambda^6$-thiomorpholin-4-yl)-4-o -tolyl-pyridin-3-yl]-N-methyl-isobutyramide.

Processes of the present invention overcome many of the disadvantages of the conventional synthetic methods by eliminating the need for expensive starting materials and avoiding use of a Grignard reaction. The overall process for preparation of compounds of formula I is shown in Scheme I.

is carried out in the presence of a base, preferably an organic base, such as triethylamine. Typical reaction conditions include refluxing the reaction mixture for about one minute, then allowing the mixture to cool to about 20° C. to about 50° C., preferably about 25° C. After cooling, the reaction mixture is stirred for about 1 to 100 hours, typically about

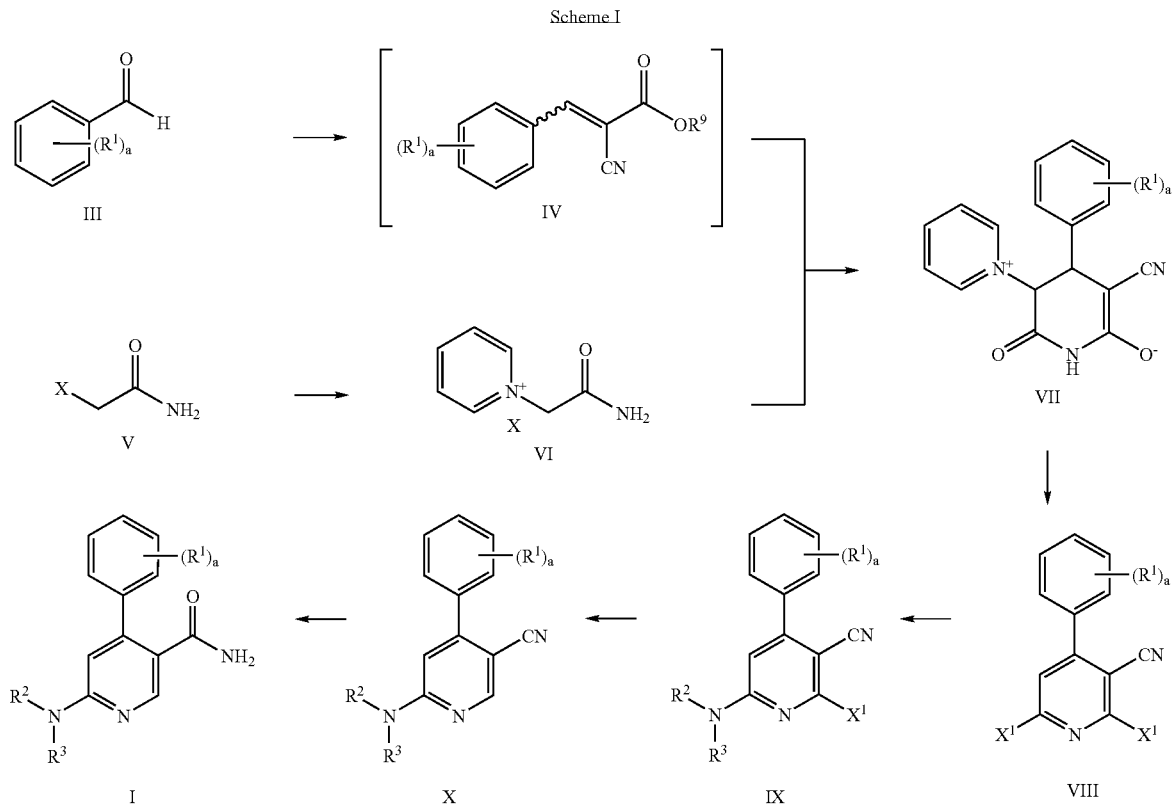

Throughout this specification, some synthetic processes for producing compounds of Formula I are often indicated by exact structures; however, it should be appreciated that processes of the present invention can be applied widely to analogous compounds of Formula I, given an appropriate consideration to protection and deprotection of reactive functional groups by methods standard to the art of organic chemistry. For example, hydroxy groups, in order to prevent unwanted side reactions, sometimes need to be converted to ethers or esters during chemical reactions at other sites in the molecule. The hydroxy protecting group is then removed to provide the free hydroxy group. Similarly, amino groups and carboxylic acid groups can be derivatized to protect them against unwanted side reactions. Typical protecting groups, and methods for attaching and cleaving them, are described fully in the above incorporated references by T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1–8 (John Wiley and Sons, 1971–1996).

Referring to Scheme I, reacting a compound of formula VI with a compound of formula IV is typically carried out in the presence of an organic solvent, such as ether, ketone, toluene or alcohol, preferably methanol. Often the reaction 66 hours. Filtration of the reaction mixture and air drying the solid then affords a pyridinium zwitter ionic compound of Formula VII.

Compound of Formula IV can be generated separated prior to its reaction with the pyridinium salt of formula VI or it can be generated in situ. In this manner, the pyridinium zwitter ionic compound of Formula VII can be produced by reacting a pyridinium salt of formula VI with a benzaldehyde compound of formula III in the presence of an α-cyanoester compound of the formula:

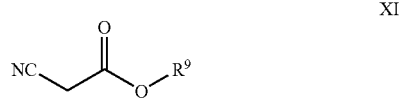

XI where R$^9$ is as defined herein. Generally the reaction is carried out in the presence of an alcohol, such as a lower alkyl alcohol, cycloalkyl alcohol, preferably isopropanol. Typically, the reaction is carried out in an organic solvent such as ether, ketone, toluene, alcohol (preferably methanol), or a mixture thereof. Often the reaction mixture includes an organic base, such as triethylamine. Typical reaction time is about 2 to 48 hours, generally about 24 hours. Suitable reaction temperature ranges from about 20° C. to 33° C., often about 25° C. to 30° C.

Referring again to Scheme I above, reacting the pyridinium zwitter ionic compound of formula VII with a reagent selected from $POCl_3$, $PBr_3$, and $(F_3CSO_2)_2O$ yields a cyanopyridine compound of formula VIII. Typical reaction conditions include heating the mixture to about 105° C. for approximately 72 hours. The mixture is then cooled to approximately 20° C. to 33° C., preferably 20° C. to 25° C. and diluted with an organic solvent, such as methylene chloride. The resulting mixture is then placed in an ice bath and stirred for about 10 minutes. Aqueous work up followed by concentration of the organic layer then affords the cyanopyridine compound of formula VIII.

The cyanopyridine compound of formula VIII is then reacted with an amine compound of the formula $HNR^2R^3$ to form a tetra-substituted pyridine compound of formula IX. Displacement of one of the $X^1$ moiety with the amine compound of the formula $HNR^2R^3$ is typically preformed in an alcoholic solvent, such as methanol. The reaction temperature is generally kept at about 0° C. to 25° C., preferably 18° C. If necessary, an ice-water bath can be used to control the reaction temperature. In one particular embodiment, the amine compound of the formula $HNR^2R^3$ is morpholine, which is added to the reaction mixture at a temperature of about 18° C. to 33° C., preferably 18° C. to 22° C. Morpholine is typically added slowly to the reaction mixture, e.g., addition time of about 10 to 60 minutes, preferably 45 minutes. The resulting mixture is stirred at about 20° C. to 33° C., preferably 20° C. to 25° C., for approximately 48 hours.

Hydrogenation of the tetra-substituted pyridine compound of formula IX in the presence of a hydrogenation catalyst then affords an amino-substituted cyanopyridine compound of formula X. Typically, the hydrogenation reaction is carried out in the presence of a base, preferably an organic base, such as triethylamine. The hydrogenation reaction temperature generally ranges from about 25° C. to 45° C., preferably 20° C. to 25° C. A variety of hydrogenation catalysts are suitable for reducing the tetra-substituted pyridine compound of formula IX. Preferred hydrogenation catalysts are transition metal based, preferably palladium metal based. A particularly useful hydrogenation catalyst is $Pd(OH)_2$ or 20% palladium hydroxide on carbon (Pearlman's catalyst). The hydrogenation reaction mixture includes an organic solvent, such as methanol. The reaction mixture is typically stirred under a high pressure of hydrogen atmosphere, typically at about 30 psi of hydrogen or higher, more generally about 40 psi of hydrogen or higher. In one particular embodiment, the hydrogenation reaction is carried out at about 48.0 to 48.3 psi of hydrogen. Generally, the reaction time ranges from about 2 to 42 hours, often about 21 hours.

The amino-substituted cyanopyridine compound of formula X is then hydrolyzed to provide a carboxamide pyridine compound of formula I. Hydrolysis of the nitrile function group of formula X can be achieved in a basic or, preferably, in an acidic medium. Exemplary acids that are useful in hydrolysis of the nitrile function group include, but are not limited to, $H_2SO_4$, HCl and acetic acid, with $H_2SO_4$ being the typical acid used in hydrolysis. Hydrolysis can be carried out in the presence or absence of an organic solvent. Typical hydrolysis reaction is carried out at a temperature in the range of about 50° C. to 140° C., preferably about 60° C. to 90° C. The reaction time generally ranges from approximately 2 to 22 hours, preferably 12 hours.

While Scheme I shows various reactions in a particular sequence, it should be appreciated that Scheme I is only an illustrative example. One skilled in the art having the present disclosure can readily recognize that some of the reaction sequences can be changed, eliminated or combined. Therefore, the scope of present invention includes all suitable variations to Scheme I reaction sequences. For example, Scheme I illustrates a reaction sequence involving substitution of one of the $X^1$ moiety of compound of formula VIII with an amine compound of the formula $HNR^2R^3$, followed by hydrogenation of compound of formula IX, then hydrolysis of the cyano group of compound of formula X to produce the carboxamide pyridine compound of formula I. However, variations of reaction sequences illustrated in Scheme I are also readily apparent to those skilled in the art having the disclosure of the present invention. For example, hydrolysis of the cyano group can be achieved prior to the reduction, i.e., hydrogenolysis, reaction.

In one particular embodiment of the present invention, each $R^1$ is independently lower alkyl, alkoxy, halogen, cyano, or alkyamino; $X^1$ is halogen; and $R^2$ and $R^3$ together with the nitrogen atom to which they are attached to form optionally substituted N-heterocyclyl.

In another embodiment of the present invention, each $R^1$ is independently lower alkyl, alkoxy, halogen, cyano and alkylamino; $X^1$ is chloro; and $R^2$ and $R^3$ together with the nitrogen atom to which they are attached to form morpholin-4-yl, 4-methyl-piperazin-1-yl, or 1,1-dioxothiomopholin-4-yl.

Another embodiment of the present invention provides various compounds that can be produced by one or more reaction disclosed herein, such compounds include, but are not limited to, methyl 2-cyano-3-(2-methylphenyl)-2-propenoate, 1-(2-amino)-2-oxoethylpyridinium chloride, 5'-cyano-1'-2',3',4'-tetrahydro-6'-hydroxy-4'-(2-methylphenyl)-2'-oxo-1,3'-bipyridium, zwitter ion, 3-cyano-2,6-dichloro-4-(2-methylphenyl)pyridine, 2-chloro-3-cyano-4-(2-methylphenyl)-6-(4-morpholinyl)pyridine, 5-cyano-4-(2-methylphenyl)-2-(4-morpholinyl)pyridine, 4-(2-methylphenyl)-6-(4-morpholinyl)-3-pyridinecarboxamide, 2-chloro-4-(2-methylphenyl)-6-(4-morpholinyl)-3-pyridinecarboxamine, 2,6-dichloro-4-(2-methylphenyl)-3-pyridinecarboxamide, 3-cyano-2,6-dichloro-4-(4-fluoro-2-methylphenyl)pyridine, 2-chloro-3-cyano-4-(4-fluoro-2-methylphenyl)-6-thiomorpholino)pyridine, 2-chloro-3-cyano-4-(4-fluoro-2-methylphenyl)-6-(1,1-dioxo-thiomorpholin-4-yl)pyridine, 4-(4-fluoro-2-methylphenyl)-6-(1,1-dioxo-thiomorpholin-4-yl)pyridine-3-carboxamide, 2-chloro-3-cyano-4-(2-methylphenyl)-6-(4-methylpiperazinyl)pyridine, 5-cyano-4-(2-methylphenyl)-2-(4-methylpiperazinyl)pyridine, and 4-(2-methylphenyl)-6-(4-methylpiperazinyl)-3-pyridinecaboxamide.

Another aspect of the present invention provides aminopyridine compound of Formula II including, but not limited to: N-(3,5-bis-trifluoromethyl-benzyl)-N-methyl-6-[methyl-(2-morpholin-4-yl-ethyl)-amino]-4-o-tolyl-nicotinamide, N-(3,5-bis-trifluoromethyl-benzyl)-N-methyl-6-morpholin-4yl-4-o-tolyl-nicotinamide, N-(3,5-bis-trifluoromethyl-benzyl)-N-methyl-6-thiomorpholin-4-yl-4-o-tolyl-nicotinamide, N-(3,5-bis-trifluoromethyl-benzyl)-N-methyl-6-(1-oxo-1$\lambda^6$-4-thiomorpholin-4-yl)-4-o-tolyl-nicotinamide, N-(3,5-Bis -trifluoromethyl-benzyl)-6-(1,1-dioxo-1$\lambda^6$-6-thiomorpholin-4-yl)-N-methyl-4-o-tolyl-nicotinamide, N-(3,5-bis-trifluoromethyl-benzyl)-N-methyl-6-piperazin-1-yl-4-o-tolyl-nicotinamide, N-(3,5-bis-trifluoromethyl-benzyl)-6-[4-(2-hydroxy-ethyl)-piperazin-1-yl)]-N-methyl-4-o-tolyl-nicotinamide, 2-(3,5-bistrifluoromethyl-phenyl)-N-[6-(4-methyl-piperazin-1-yl)-4-o-tolyl-pyridin-3-yl]-N-methyl-isobutyramide, 2-(3,5-bis-trifluoromethyl-phenyl)-N-(6-morpholin-4-yl-4-o-tolyl-pyridin-3-yl)-N-methyl-isobutyramide, 2-(3,5-bis-trifluoromethyl-phenyl)-N-[4-(4-fluoro-2-methyl-phenyl)-6-(4-methyl-piperazin-1-yl)-pyridin-3-yl]-N-methyl-isobutyramide, 2-(3,5-bis-trifluoromethyl-phenyl)-N-[4-(2-chloro-phenyl)-pyridin-3-yl]-N-methyl-isobutyramide, 2-(3,5-bis-trifluoromethyl-phenyl)-N-methyl-N-(4-o-tolyl-pyridin-3-yl)-isobutyramide, 2-(3,5-bis-trifluoromethyl-phenyl)-N-methyl-N-[6-(4-pyridin-2-yl-piperazin-1-yl)4-o-tolyl-pyridin-3-yl)-isobutyramide, 2-(3,5-bis-trifluoromethyl-phenyl)-N-(6-morpholin-4-yl-4-o-tolyl-pyridin-3-yl)-isobutyramide, 2-(3,5-bis-trifluoromethyl-phenyl)-N-[4-(2-chloro-phenyl)-6-dimethylamino-pyridin-3-yl]-isobutyramide, 2-(3,5-bis-trifluoromethyl-phenyl)-N-methyl-N-(6-piperazin-1-yl-4-o-tolyl-pyridin-3-yl)-isobutyramide, and 2-(3,5-bis-trifluoromethyl-phenyl)-N-[6-(1,1-dioxo-1$\lambda^6$-thiomorpholin-4-yl)-4-o-tolyl-pyridin-3-yl]-N-methyl-isobutyramide.

Additional objects, advantages, and novel features of this invention will become apparent to those skilled in the art upon examination of the following examples thereof, which are not intended to be limiting.

EXAMPLES

Example 1

This example illustrates a process for preparing 4-fluoro-2-methylbenzaldehyde (Fig. III, Scheme I)

2-Bromo-5-fluorotoluene (37.5 mL, 56.1 g, 297 mmol) was dissolved in 500 mL of dry THF and the solution was cooled to −78° C. Butyllithium in hexanes (2.5 M) (119 mL, 297 mmol, 1.0 equiv) was added at −75 to −78° C. over 35 minutes, and the resulting mixture was stirred at −78° C. for 20 minutes. Dry N,N-dimethylformamide (27.6 mL, 26.0 g, 356 mmol, 1.2 equiv) was added over 26 minutes at −75 to −78° C. The resulting solution was stirred at −78° C. for 60 minutes then allowed to warm to 15° C. over 2 hours.

Ammonium chloride (100 g of 15.9% aqueous solution) was added over 5 minutes at 15–20° C. The solution was concentrated by fractional distillation (597 mL collected at 50–61° C.). The distillation pot layers were separated. The aqueous layer was extracted three times with 25 mL of methyl tert-butyl ether (i.e., MTBE). The organic layers were combined, washed with 50 mL of brine, dried (MgSO$_4$), filtered, and fractionally distilled (b.p. 54–62° C.) to yield 59.3 g of yellow oil. The oil was fractionally distilled (b.p. 60–62° C. at 1.6–2.0 mmHg of pressure) to afford 28.041 g (68.4%) of a colorless oil.

Example 2

This example illustrates a process for preparing methyl 2-cyano-3-(2-methylphenyl)-2-propenoate (Fig. IV, Scheme I)

A 100-mL, 1-necked round bottom flask (with magnetic stir-bar and dry N$_2$ adaptor) was charged with 11.6 mL (12.0 g, 100 mmol) of o-tolualdehyde, 8.8 mL (9.9 g, 100 mmol) of methyl cyanoacetate, and 50 mL of isopropanol. Morpholine (0.50 mL, 0.55 g, 6.3 mmol, 6.3 mol %) was added and the mixture was stirred at 20–33° C. for 60 minutes. This mixture was diluted with 25 mL of isopropanol. The precipitate was filtered, washed with 10 mL of isopropanol, and dried to afford 17.37 g (86.3%) of methyl 2-cyano-3-(2-mehtylphenyl)-2-propenoate as a colorless solid.

Example 3

This example illustrates a process for preparing 1-(2-amino)-2-oxoethylpyridinium chloride (Fig. VI, Scheme I)

A 3-L, 4-necked round bottom flask (with reflux condenser/dry N$_2$ adaptor, perforated Teflon paddle stirrer with glass shaft, septum with Teflon-coated thermocouple, and Teflon stopper) was charged with 190.76 g (2.04 mol) of 2-chloroacetamide, 2.0 L of n-butyl acetate and 192 mL (187.8 g, 2.37 mol) of dry pyridine. The resulting mixture was refluxed for 24 hours, and then cooled to 25° C. The precipitate was filtered, washed with 500 mL of n-butyl acetate and twice with 500 mL of hexanes, and dried to afford 324.05 g (92.0%) of 1-(2-amino)-2-oxoethylpyridinium chloride as a beige colored solid.

Example 4

This example illustrates another process for preparing 1-(2-amino)-2-oxoethylpyridinium chloride (Fig. VI, Scheme I).

A 2000-mL pressure bottle with paddle stirrer was charged with 93.51 g (1.00 mol) of 2-chloroacetamide, 300 mL of isopropanol, and 82.4 niL (80.7 g, 1.02 mol) of pyridine. The resultant mixture was refluxed for 18 hours, and then cooled to 25° C., and the title compound was isolated as described in Example 3.

Example 5

This example illustrates a process for preparing 1',2',3',4'-tetrahydro-5'-cyano-6'-hydroxy-4'(2-methylphenyl)-2'-oxo-1,3'-bipyridinium, zwitter ion (Fig. VII, Scheme I)

A 100-mL, 2-necked round bottom flask equipped with a reflux condenser was charged with 1.726 g (10.0 mmol) of the pyridinium salt (i.e., 1-(2-amino)-2-oxoethylpyridinium chloride, see Example 3 or 4), 2.012 g (10.0 mmol) of methyl 2-cyano-3-(2-methylphenyl)-2-propenoate (see Example 2), 20 mL of methanol, and triethylamine (1.55 mL, 1.11 g, 1.10 equiv). The mixture was refluxed for 1 minute then allowed to cool to 25° C. and stirred for 66 hours. The precipitate was filtered, washed successively with 10 mL of methanol, 10 mL of toluene and 10 mL of hexanes, and dried to afford 2.734 g (89.5%) of 1',2',3',4'-tetrahydro-5'-cyano-6'-hydroxy-4'(2-methylphenyl)-2'-oxo-1,3'-bipyridinium, zwitter ion as a bright yellow solid.

Example 6

This example illustrates another process for preparing 1',2',3',4'-tetrahydro-5'-cyano-6'-hydroxy-4'(2-methylphenyl)-2'-oxo-1,3'-bipyridinium, zwitter ion (Fig. VII, Scheme I)

A 3000-mL, 4-necked flask (with a 250-mL pressure equilibrating addition funnel/dry N$_2$ adapter, spetum with Teflon-coated thermocouple, Teflon paddle stirrer/glass shaft, and stopper) was charged with 115.6 mL (120.15 g, 1.0 mol) of o-tolualdehyde, 87.9 mL (90.09 g, 1.0 mol) of methyl cyanoacetate, 172.61 g (1.0 mol) of the pyridinium salt of Example 3 and 2.0 L of methanol. The addition funnel was charged with 153.3 mL (111.3 g, 1.1 mol) of triehtylamine and was added to the reaction mixture over a period of 20 minutes at 20–25° C. The resulting mixture was stirred at 25–30° C. for 24 hours. The precipitate was filtered, washed successively with 500 mL of methanol, 500 mL of toluene and 500 mL of hexanes, and dried to afford 285.10 g (93.4%) of 1',2',3',4'-tetrahydro-5'-cyano-6'-hydroxy-4'(2-methylphenyl)-2'-oxo-1,3'-bipyridinium, zwitter ion as a bright yellow solid.

Example 7

This example illustrates another process for preparing 1',2',3',4'-tetrahydro-5'-cyano-6'-hydroxy-4'(2-methylphenyl)-2'-oxo-1,3'-bipyridinium, zwitter ion (Fig. VII, Scheme I)

A 3000-mL, 4-necked flask (equipped with a 250 mL pressure equilibrating addition funnel/dry $N_2$ adapter, septum with Teflon-coated thermocouple, Teflon paddle stirrer/glass shaft, and stopper) was charged with 115.6 mL (120.15 g, 1.0 mol) of o-tolualdehyde, 87.9 mL (99.09 g, 1.0 mol) of methyl cyanoacetate, 172.61 g (1.0 mol) of pyridinium salt of Example 3, 300 mL of isopropanol, and 1.7 L of methanol. The addition funnel was charged with 153.3 mL (111.3 g, 1.1 mol) of triethylamine and was added to the reaction mixture over a period of 24 minutes at 20–25° C. The resulting mixture was stirred at 25–30° C. for 24 hours.

The precipitate was filtered, washed successively with 500 mL of methanol, 500 mL of toluene and 500 mL of hexanes, and dried to afford 284.69 g (93.2%) of 1',2',3',4'-tetrahydro-5'-cyano-6'-hydroxy-4'(2-methylphenyl)-2'-oxo-1,3'-bipyridinium, zwitter ion as a bright yellow solid. An analytical sample tested revealed: m.p. 232–233° C. (dec); $^1$H NMR (DMSO-$d_6$) δ 9.82 (s, 1H), 8.98 (d, 2H), 8.50 (t, 1H), 8.04 (t, 2H), 7.45 (br, 1H), 7.12 (t, J=7.0 Hz, 1H), 6.99 (t, J=7.0 Hz, 1H), 6.93 (d, J=8.0 Hz, 1H), 6.13 (d, J=13 Hz, 1H), 6.82 (d, J=13 Hz, 1H), 2.08 (s, 3H); $^{13}$C NMR (DMSO-$d_6$) δ 166.4, 163.8, 147.3, 145.8, 137.2, 137.0, 128.3, 128.1, 127.5, 126.9, 126.0, 75.3, 53.6, 19.8; IR (KBr) 3625–3300, 3162, 3135, 3045, 2956, 2929, 2168, 1701, 1634 1600 cm$^{-1}$. Analytically calculated for $C_{18}H_{15}N_2O_2$: C, 70.81; H, 4.95; N, 13.76; Cl, 26.95. Found: C, 70.66; H, 5.10; N, 13.80.

Example 8

This example illustrates a process for preparing 5'-cyano-1',2',3',4'-tetrahydro-6'-hydroxy-4'(2-methyl-4-fluorophenyl)-2'-oxo-1,3'-bipyridinium, zwitter ion (Fig. VII, Scheme I).

A 1000 mL, 4-necked flask (with 50 mL pressure equilibrating addition funnel/dry $N_2$ adapter, septum with teflon-coated thermocouple, teflon paddle stirrer/glass shaft, and stopper) was charged with 28.01 g (203 mmol) of 4-fluoro-2-methylbenzaldehyde, 17.8 mL (20.1 g, 203 mmol) of methyl cyanoacetate, 35.00 g (203 mrnol) of N-(carbamoylmethyl)-pyridinium chloride, and 400 mL of methanol. The addition funnel was charged with 31.1 mL (22.6 g, 223 mmol) triethylamine and was added to the reaction mixture over 11 min at 170 rpm and 20–25° C. (intermittent ice-water bath). The resulting mixture was stirred at 25–30° C. for 24 h.

The precipitate was suction filtered using a 600 mL coarse sintered glass funnel. The precipitate was washed successively with 100 mL of 25° C. methanol, 100 mL of 25° C. toluene, and 100 mL of 25° C. hexanes. The solid was then air dried 3.5 h at 25° C. to afford 60.69 g (92.6%) of bright yellow solid, m.p. 236–237° C. (dec); $^1$H NMR (DMSO $d_6$) δ 9.84 (s, 1H), 8.98 (d, J=6.0 Hz, 2H), 8.52 (t, J=7.5 Hz, 1H), 8.07 (dd, 2H), 7.50 (br, 1H), 6.97 (br t, 7.0 Hz, 1H), 6.80 (dd, J=1.5 Hz, J=10 Hz, 1H), 6.26 (d, J=13 Hz, 1H), 4.81 (d, J=13 Hz, 1H), 2.08 (br, 3H); $^{13}$C NMR (DMSO $d_6$)δ 166.3, 163.7, 161.2 (d, J=241.9 Hz), 147.4, 145.8, 139.9, 133.4, 130.3, 128.5, 126.0, 117.4, 113.7, 75.2, 53.6, 31.4, 19.7; IR (KBr) 3170, 3130, 3045, 2168, 1703, 1633, 1602, 1577 cm$^{-1}$. Elem. Anal. Calcd for $C_{18}H_{14}FN_3O_2$: C, 66.87; H, 4.36; F, 5.88; N, 13.00. Found: C, 66.31; H, 4.29; F, 6.05; N, 12.72.

Example 9

This example illustrates a process for preparing 3-cyano-2,6-dichloro-4-(2-methylphenyl)pyridine (Fig. VIII, Scheme I)

A mixture of 40.00 g (131.0 mmol) of the appropriate pyridinium zwitter ion (prepared according to Example 5, 6 or 7) and 50.0 mL (82.3 g, 536 mmol) of phosphorus oxychloride was heated in a 300-mL Parr bottle at 135° C. for 10 hours.

The reaction mixture was cooled to 25° C. and diluted with 75 mL of methylene chloride. The solution was transferred onto 350 g of ice. Additional methylene chloride (25 mL) was used to aid the transfer. The resulting mixture was stirred for 1 hour. The layers were separated, and the aqueous layer was extracted twice with 25 mL of methylene chloride and twice with 50 mL of toluene. The extracts were combined, dried (5.0 g $Na_2SO_4$), and filtered through 15 g of Filtrol® on a 60-mL coarse sintered glass funnel. The flask and the solid were washed with 50 mL of toluene. The combined mother liquors were concentrated to afford 28.70 g (83.3%) of 3-cyano-2,6-dichloro-4-(2-methylphenyl)pyridine as a near colorless solid (LC assay 100.7 wt %).

An analytical sample was prepared by recrystallization from isopropanol and revealed: m.p. 129–131° C.; $^1$H NMR (CDCl$_3$) δ 7.43 (dt, J=1.5 Hz, J=7 Hz, 1H), 7.37–7.31 (m, 2 H), 7.33 (s, 1H), 7.18 (dd, J=1.5 Hz, 8 Hz, 1H), 2.25 (s,3H); $^{13}$C NMR (CDCl$_3$) δ 159.1, 153.9, 153.3, 135.3, 134.1, 131.3, 130.7, 128.8, 126.7, 124.5, 113.7, 110.3, 20.0; IR (KBr) 3087, 2227, 1603, 1569, 1520, 1340 cm$^{-1}$. Analytically calculated for $C_{13}H_8Cl_2N_2$: C, 59.34; H, 3.06; N, 10.65; Cl, 26.95. Found: C, 59.00; H, 3.05; N, 10.64; Cl, 27.76.

Example 10

This example illustrates a process for preparing 3-cyano-2,6-dichloro-4-(4-fluoro-2-methylphenyl)pyridine (Fig. VIII, Scheme I)

A mixture of 55.00 g (170.1 mmol) of the appropriate pyridinium zwitter ion (prepared according to Example 5, 6 or 7) and 65 mL (106.9 g, 697 mmol, 4.1 equiv) of phosphorus oxychloride was heated in a 300-mL Parr bottle at 135° C. for 12 hours.

The reaction mixture was cooled to 25° C., diluted with 200 mL of methylene chloride, transferred using additional 25 mL of methylene chloride onto 450 g of ice, and stirred until all the ice melted. The layers were separated, and the aqueous layer was extracted successively twice with 25 mL of methylene chloride and twice with 125 mL of toluene. The combined extracts were filtered through 15 g of Filtrol® on a 60-mL coarse sintered glass funnel. The flask and the solid were washed with 100 mL of toluene. The combined mother liquors were concentrated to afford 39.70 g (83.0%) of near colorless solid.

An analytical sample was prepared by recrystallization from isopropanol and revealed: m.p. 161.5–162.5° C.; $^1$H NMR (CDCl$_3$) δ 7.32 (s, 1H), 7.18 (dd, J=5.5 Hz, J=8.5 Hz, 1H), 7.08 (dd, J=2.5 Hz, J=9.5 Hz, 1H), 7.04 (dt, J=2.5 Hz, J=8–8.5 Hz, 1H), 2.26 (s, 3H); $^{13}$C NMR (CDCl$_3$) δ 163.9 (d, J=250 Hz), 158.0, 154.0, 153.4, 138.4 (d, J=8.4 Hz), 130.8 (d, J=8.8 Hz), 130.1 (d, J=3.6 Hz), 124.6, 118.2 (d, J=21.6 Hz), 114.0 (d, J=21.6 Hz), 113.6, 110.4, 20.2 (d, J=1.6 Hz); IR (KBr) 3100, 2920, 2230, 1590, 1578, 1566, 1521, 1496 cm$^{-1}$. Analytically calculated for $C_{13}H_7Cl_2FN_2$: C, 55.54; H, 2.51; F, 6.76; N, 9.97. Found: C, 55.32; H, 2.55; F, 7.02; N, 9.78.

Example 11

This example illustrates a process for preparing 2-chloro-3-cyano-4-(2-methylphenyl)-6-(4-morpholinyl)pyridine (Fig. VIII, Scheme I)

The crude dichloride, 3-cyano-2,6-dichloro-4-(2-methylphenyl)pyridine, (194.8 g, 0.740 mol, see Example 8) and 1100 mL of methanol were added to a 2000-mL, 3-necked flask (equipped with a 125-mL pressure-equilibrating addition funnel/dry $N_2$ adapter, septum with teflon-coated thermocouple, and teflon paddle stirrer/glass shaft). The mixture was cooled to 18° C. Morpholine (132.3 mL, 132.2 g, 1.52 mol) was charged to the addition funnel and added dropwise to the reaction mixture over a period of 45 minutes. The resulting mixture was stirred at 20–25° C. for 18 hours.

The precipitate was filtered, washed successively with 150 mL of methanol and 1000 mL of water, and dried to afford 182.04 g (78.4%) of 2-chloro-3-cyano-4-(2-methylphenyl)-6-(4-morpholinyl)pyridine as a colorless solid.

An analytical sample was prepared by recrystallization from isopropanol and revealed: m.p. 152–154° C.; $^1$H NMR (CDCl$_3$) δ 7.35 (dt, J=1.5 Hz, J=7.5 Hz, 1H), 7.31–7.28 (m, 1H), 7.26 (dd, J=1.5 Hz, J=7.5 Hz, 1H), 6.37 (s, 1H), 3.81–3.79 (m, 4H), 3.68–3.66 (m, 4H), 2.25 (s, 3H); $^{13}$C NMR (CDCl$_3$) δ 158.3, 156.9, 153.0, 136.4, 135.1, 130.6, 129.5, 128.4, 126.1, 115.8, 104.7, 97.8, 66.4. 44.8, 19.7; IR (KBr) 2966–2843, 2216, 1597, 1490 cm$^{-1}$. Analytically calculated for $C_{17}H_{16}ClN_3O$: C, 65.07; H, 5.14; N, 13.39; Cl, 11.30. Found: C, 65.38; H, 5.28; N, 13.36; Cl, 11.65.

Example 12

This example illustrate a process for preparing 2-chloro-3-cyano-4-(2-methylphenyl)-6-(4-methylpiperazinyl)pyridine (Fig. IX, Scheme I).

Crude dichloride, 3-cyano-2,6-dichloro-4-(2-methylphenyl)pyridine, (78.00 g, 0.296 mol) and 330 mL of methanol were added to a 1000-mL, 3-necked flask (equipped with a 125 mL pressure-equilibrating addition funnel/dry $N_2$ adapter, septum with teflon-coated thermocouple, and teflon paddle stirrer/glass shaft), and the mixture was cooled to 18° C. 1-Methylpiperazine (67.3 mL, 60.78 g, 0.607 mol) was charged to the addition funnel and added dropwise to the reaction mixture at 18–22° C. over a period of 15 minutes. Seed crystals of 2-chloro-3-cyano-4-(2-methylphenyl)-6-(4-methylpiperazinyl)pyridine were added after 2 hours and the suspension was stirred at 20–25° C. for an additional 18 hours.

Water (165 mL) was added dropwise over 1 hour and the resulting mixture was stirred at 25° C. for 3 hours. The precipitate was filtered, washed successively with 90 mL of 2:1 methanol-H$_2$O and 100 mL of water, and dried to afford 74.19 g (76.6%) of 2-chloro-3-cyano-4-(2-methylphenyl)-6-(4-methylpiperazinyl)pyridine as a beige solid.

An analytical sample was prepared by recrystallization from isopropanol and revealed: m.p. 116–123° C.; $^1$H NMR (CDCl$_3$) δ 7.34 (dt, J=7.5 Hz, J=1.5 Hz, 1H), 7.3–7.25 (m, 2H), 7.14 (dd, J=7.5 Hz, J=1.5 Hz, 1H), 6.37 (s, 1H), 3.71 (br m, 4H), 2.49 (br t, 4H), 2.35 (s, 3H), 2.25 (s, 3H); $^{13}$C NMR (CDCl$_3$) δ 158.4, 156.9, 153.2, 136.8, 135.4, 130.9, 129.6, 128.7, 126.3, 116.2, 105.0, 97.3, 54.7, 46.3, 44.8, 20.0; IR (KBr) 2966, 2936, 2846, 2797, 2215, 1592, 1498 cm$^{-1}$. Analytically calculated for $C_{18}H_{19}ClN_4$: C, 66.15; H, 5.86; N, 17.14; Cl, 10.85. Found: C, 66.04; H, 6.04; N, 17.11; Cl, 10.94.

Example 13

This example illustrates a process for preparing 2-chloro-3-cyano-4-(4-fluoro-2-methylphenyl)-6-(thiomorpholino)pyridine (Fig. IX, Scheme I).

Crude 3-cyano-2,6-dichloro-4-(4-fluoro-2-methylphenyl)pyridine, (32.44 g, 115.4 mmol) and 300 mL of methanol were added to a 500-mL, 3-necked flask (equipped with a 25-mL pressure-equilibrating addition funnel/dry $N_2$ adapter, septum with teflon-coated thermocouple, and teflon paddle stirrer/glass shaft). Thiomorpholine (23.0 mL, 25.0 g, 242 mmol, 2.10 equiv) was added dropwise over a period of 22 minutes via the addition funnel, and the resulting mixture was stirred at 20–25° C. for 18 hours. The precipitate was filtered, washed with 30 mL of methanol, and dried to afford 35.47 g (88.4%) of 2-chloro-3-cyano-4-(4-fluoro-2-methylphenyl)-6-(thiomorpholino)pyridine as a beige solid.

An analytical sample was prepared by recrystallization from ethanol and revealed: m.p. 195.3–197.3° C.; $^1$H NMR (CDCl$_3$) δ 7.13 (dd, J=5.5 Hz, J=8.5 Hz, 1H), 7.01 (dd, J=3.0 Hz, J=10 Hz, 1H), 6.97 (dt, J=3.0 Hz, J=8.5 Hz, 1H), 6.33 (s, 1H), 4.04 (br, 4H), 2.70 (br t, J=5.0 Hz, 4H), 2.25 (s, 3H); $^{13}$C NMR (CDCl$_3$) δ 163.3 (d, J=247 Hz), 157.7, 156.2, 153.4, 138.3 (d, J=8.5 Hz), 132.7 (d, J=3.1 Hz), 130.5 (d, J=8.5 Hz), 117.7 (d, J=21.3 Hz), 116.0, 113.4 (d, J=21.6 Hz), 105.3, 97.5, 48.1, 27.0, 20.2 (d, J=1.6 Hz); IR (KBr) 2219, 1594, 1581, 1502, 1489, 1448, 1432 cm$^{-1}$. Analytically calculated for $C_{17}H_5CFN_3S$: C, 58.70; H, 4.35; N, 12.08. Found: C, 58.76; H, 4.43; N, 12.04.

Example 14

This example illustrates a process for preparing 2-chloro-3-cyano-4-(4-fluoro-2-methylphenyl)-6-(1,1-dioxo-thiomorpholin-4-yl)pyridine (Fig. IX, Scheme I).

Oxone® (56.18 g, 91.4 mmol) was added to a solution of 2-chloro-3-cyano-4-(4-fluoro-2-methylphenyl)-6-(thiomorpholino)pyridine (26.54 g, 76.3 mmol) in 200 mL of NMP in a 1000-mL, 3-necked flask (equipped with a teflon paddle stirrer, septum with teflon-coated thermocouple, dry $N_2$ adapter). The mixture was stirred at 25° C. for 20 hours, and diluted with 800 mL of water. The resulting mixture was stirred at 25° C. for 30 minutes. The precipitate was filtered, washed several times with H$_2$O, and dried to afford 29.30 g (101.1%) of 2-chloro-3-cyano-4-(4-fluoro-2-methylphenyl)-6-(1,1-dioxo-thiomorpholin-4-yl)pyridine as a colorless solid.

An analytical sample was prepared by recrystallization from acetonitrile and revealed: m.p. 264–267° C. $^1$H NMR (DMSO-d$_6$) δ 7.30 (dd, J=5.5–6 Hz, J=8.8 Hz, 1 H), 7.26 (dd, J=2.5 Hz, J=10 Hz, 1H), 7.17 (dd, J=2.5 Hz, J=8.5–9.0 Hz, 1H), 7.07 (s, 1H), 4.15 (m, 4H), 3.22 (br, 4H), 2.22 (s, 3H); $^{13}$C NMR (DMSO-d$_6$) δ 163.1 (d, J=244 Hz), 158.2, 155.8, 152.1, 139.1 (d, J=8.4 Hz), 133.3 (d, J=2.9 Hz), 131.6 (d, J=8.8 Hz), 117.6 (d, J=21.3 Hz), 116.4, 113.6 (d, J=21.3 Hz), 107.9, 97.5, 51.2, 44.1, 20.1; IR (KBr) 2930, 2223, 1588, 1522, 1500, 1494, 1474, 1429, 1125 cm$^{-1}$. Analytically calculated for $C_{17}H_{15}ClFN_3O_2S$: C, 53.76; H, 3.98; N, 11.06. Found: C, 53.76; H, 3.94; N, 11.06.

Example 15

This example illustrates a process for preparing 5-cyano-4-(2-methylphenyl)-2-(4-morpholinyl)pyridine (Fig. X, Scheme I).

A mixture of 20.00 g (63.74 mmol) of 2-chloro-3-cyano-4-(2-methylphenyl)-6-(4-morpholinyl)pyridine, 9.77 mL (7.10 g, 70.11 mmol, 1.1 equiv) of triethylamine, 33.9 mg Pd(OH)$_2$ or 249 mg (0.242 mmol, 0.379 mol %) of 20% palladium hydroxide on carbon [Pearlman's catalyst, 32.2% LOD], and 80 mL of methanol was stirred in a 300-mL Parr bottle at 25° C. and 48.0–41.3 psi of hydrogen for 21 hours.

The pressure was vented and the mixture diluted with 40 mL of H$_2$O. The mixture was transferred to a round bottom flask using 40 mL of methanol. The mixture was concentrated and the residue was diluted with 80 mL of toluene and filtered through 2.0 g Celite®. Celite® was washed three times with 10 mL of toluene. A solution of 2.80 g (70.1 mmol) sodium hydroxide in 5 mL of H$_2$O was added to the combined mother liquors. The layers were separated and the aqueous layer (pH=13–14) was extracted three times with 20 mL of toluene. The organic layers were combined and concentrated to afford 17.95 g of 5-cyano-4-(2-methylphenyl)-2-(4-morpholinyl)pyridine as a colorless solid (LC assay 91.8–93.9 wt %) (yield 92.6–94.7%).

An analytical sample was prepared by radial chromatography on silica gel followed by recrystallization from isopropanol and revealed: m.p. 128.5–129.7° C.; $^1$H NMR (CDCl$_3$) δ 8.48 (s, 1H), 7.35 (dt, J=1.5 Hz, J=7.5 Hz, 1H), 7.31–7.29 (m, 1H), 7.28–7.26 (M, 1H), 7.16 (dd, J=1.5 Hz, J=7.5 Hz, 1H), 6.48 (d, 1H), 3.82–3.80 (m, 4H), 3.68–3.66 (m, 4H), 2.25 (s, 3H); $^{13}$C NMR (CDCl$_3$) δ 159.6, 154.0, 153.1, 136.8, 135.2, 130.6, 129.2, 128.7, 126.0, 117.9, 106.3, 98.4, 66.5, 44.8, 19.7; IR (KBr) 2967, 2892, 2853, 2210, 1593, 1503, 1444 cm$^{-1}$. Analytically calculated for C$_{17}$H$_{17}$N$_3$O: C, 73.10; H, 6.13; N, 15.04. Found: C, 73.40; H, 6.18; N, 15.03.

Example 16

This example illustrates a process for preparing 5-cyano-4-(2-methylphenyl)-2-(4-methylpiperazinyl)pyridine (Fig. X, Scheme I).

A mixture of 2-chloro-3-cyano-4-(2-methylphenyl)-6-(4-methylpiperazinyl)-pyridine (20.00 g, 61.19 mmol), 9.38 mL (6.81 g, 67.3 mmol, 1.1 equiv) of triethylamine, 25.8 mg Pd(OH)$_2$ or 190 mg (0.184 mmol, 0.300 mol %) of 20% palladium hydroxide on carbon [Pearlman's catalyst, 32.2% LOD], and 80 mL of methanol was stirred in a 300-mL Parr bottle at 25° C. and 48.3–43.0 psi hydrogen for 10 hours.

The pressure was vented and the mixture was diluted with 40 mL of H$_2$O. The mixture was transferred to a round bottom flask using 40 mL of methanol. Volatiles were removed on a rotary evaporator at 35° C. and 60–30 mm Hg. The resulting residue was diluted with 80 mL of toluene, and filtered through a pad of 2.0 g of Celite®. The Celite® was washed three times with 10 mL of toluene. A solution of 2.80 g (70.1 mmol) sodium hydroxide in 5 mL of H$_2$O was added to the combined mother liquors. The layers were separated and the aqueous layer (pH=13–14) was extracted three times with 20 mL of toluene. The combined organic layers were concentrated in vacuo (rotary evaporator at 35° C. and 30 mm Hg). The residual yellow syrup was taken up in 100 mL of toluene, washed with dilute HCl (20.5 mL, 20 mL H$_2$O with 0.5 mL 12 N HCl), washed with 20 mL of H$_2$O, then concentrated to afford 16.85 g (94.2%) of 5-cyano-4-(2-methylphenyl)-2-(4-methylpiperazinyl)pyridine as a near-colorless solid.

An analytical sample was prepared by recrystallization from isopropanol and revealed: m.p. 109.5–110.4° C.; $^1$H NMR (CDCl$_3$) δ 8.46 (s, 1H), 7.34 (t, J=7 Hz, 1H), 7.30 (d, J=7 Hz, 1H), 7.26 (t, J=7.5 Hz, 1H), 7.16 (dd, J=7.5 Hz, 1H), 6.49 (s, 1H), 3.72 (br t, 4H), 2.50 (t, J=5 Hz, 4H), 2.35 (s, 3H), 2.25 (s, 3H); $^{13}$C NMR (CDCl$_3$) δ 159.7, 154.0, 153.4, 137.2, 135.5, 130.8, 129.3, 128.9, 126.2, 118.3, 106.6, 98.0, 54.9, 46.4, 44.7, 20.0; IR (KBr) 3019, 2936, 2884, 2848, 2793, 2210, 1607, 1590, 1504 cm$^{-1}$. Analytically calculated for C$_{18}$H$_{20}$N$_4$: C, 73.94; H, 6.90; N, 19.16. Found: C, 74.04; H, 7.03; N, 18.98.

Example 17

This example illustrates a process for preparing 5-cyano-4-(4-fluoro-2-methylphenyl)-2-(1,1-dioxo-thiomorphlin-4-yl)pyridine (Fig. X, Scheme I).

A 300-mL Parr bottle charged with crude 2-chloro-3-cyano-4-(4-fluoro-2-methylphenyl)-6-(1,1-dioxo-thiomorpholin-4-yl)pyridine (19.86 g, 52.29 mmol), 10.9 mL (7.94 g, 78.4 mmol, 1.50 equiv) of triethylamine, 220 mg Pd(OH)$_2$ or 1.62 g (1.57 mmol, 3.0 mol %) of 20% palladium hydroxide on carbon [Pearlman's catalyst, 32.2% LOD] and 100 mL of dry DMF. The mixture was stirred at 25° C. and 48.9–43.2 psi of H$_2$ for 25.5 hours. The pressure was vented, and the mixture was filtered through a 5.0 g pad of cellulose. The cellulose pad was washed with 10 mL of DMF. Water (400 mL) was added to the filtrate and the resulting mixture was stirred for 30 minutes. The precipitate was filtered, washed several times with H$_2$O, and dried to afford 17.52 g (97.0%) of 5-cyano-4-(4-fluoro-2-methylphenyl)-2-(1,1-dioxo-thiomorphlin-4-yl)pyridine as a slightly grey solid (97% conversion).

A 300-mL Parr bottle was charged with 17.31 g of crude 5-cyano-4-(4-fluoro-2-methylphenyl)-2-(1,1-dioxo-thiomorphlin-4-yl)pyridine, 7.3 mL (5.30 g, 52.4 mmol) of triethylamine, 148 mg Pd(OH)$_2$ or 1.09 g (1.05 mmol) of 20% palladium hydroxide on carbon [Pearlman's catalyst, 32.2% LOD] and 100 mL of dry DMF. The mixture was stirred at 25° C. and 42.5–28.2 psi hydrogen for 23 hours. The pressure was vented and the mixture was filtered through a 5.0 g pad of cellulose. The cellulose pad was washed with 10 mL of DMF. Water (400 mL) was added to the filtrate and the resulting mixture was stirred at 25° C. for 30 minutes. The precipitate was filtered, washed several times with H$_2$O, and dried to afford 17.04 g (95.5%) of 5-cyano-4-(4-fluoro-2-methylphenyl)-2-(1,1-dioxo-thiomorphlin-4-yl)pyridine as a colorless solid (100% conversion).

An analytical sample was prepared by recrystallization from acetonitrile and revealed: m.p. 219.5–220.5° C.; $^1$H NMR (CDCl$_3$) δ 8.52 (d, J=1 Hz, 1H), 7.14 (dd, J=5.5 Hz, J=8.5 Hz, 1H), 7.04 (dd, J=2.5 Hz, J=9.5 Hz, 1H), 7.00 (dd, J=2.5 Hz, J=8.5 Hz, 1H), 6.61 (d, J=1 Hz, 1H), 4.27 (br t, 4H), 3.10 (br t, 4H), 2.24 (s, 3H); $^{13}$C NMR (CDCl$_3$) δ 163.4 (d, J=248 Hz), 157.9, 154.4, 153.6, 138.2 (d, J=8.0 Hz), 132.5 (d, J=3.3 Hz), 130.7 (d, J=8.8 Hz), 117.8 (d, J=21.6 Hz), 117.2, 113.5 (d, J=21.6 Hz), 107.2, 100.6, 51.6, 43.8, 20.2; IR (KBr) 2930, 2217, 1599, 1531, 1494, 1432, 1123, 1117 cm$^{-1}$. Analytically calculated for C$_{17}$H$_{16}$FN$_3$O$_2$S: C, 59.12; H, 4.67; N, 12.17. Found: C, 59.19; H, 4.69; N, 12.17.

Example 18

This example illustrates a process for preparing 4-(2-methylphenyl)-6-(4-morpholinyl)-3-pyridinecarboxamide (Fig. I, Scheme I).

A mixture of 5-cyano-4-(2-methylphenyl)-2-(4-morpholinyl)pyridine (17.71 g), 18 mL of toluene, and 17.0 mL (33.1 g, 319 mmol) of concentrated sulfuric acid was heated at 70° C. for 12 hours, cooled to room temperature, and quenched by addition of 100 mL of cold $H_2O$. Ethyl acetate (100 mL) was added followed by a solution of 25.5 g (638 mmol) of sodium hydroxide in 50 mL of $H_2O$. The aqueous layer was separated and extracted three times with 50 mL of ethyl acetate. The organic layers were combined and concentrated to afford 19.14 g of 4-(2-methylphenyl)-6-(4-morpholinyl)-3-pyridinecarboxamide as a colorless solid (LC assay 87.7 wt %) (yield 94.9–97%).

An analytical sample was prepared by filtration through a plug of silica gel and recrystallization from ethyl acetate and revealed: m.p. 144–145.5° C.; $^1$H NMR (CDCl$_3$) δ 8.93 (s, 1H), 7.36 (dt, J=1.5 Hz, J=7.5 Hz, 1H), 7.32–7.29 (m, 2H), 7.21–7.20 (m, 1H), 6.30 (s, 1H), 5.6 (br, 1H), 5.1 (br, 1H), 3.82–3.80 (m, 4H), 3.64–3.62 (m, 4H), 2.15 (s, 3H); $^{13}$C NMR (CDCl$_3$) δ 168.0, 160.1, 151.8, 149.5, 139.0, 135.8, 130.7, 129.0, 128.2, 126.5, 117.6, 106.2, 66.6, 45.0, 19.8; IR (KBr) 3462, 3300–3000, 2959, 2854, 1660, 1584, 1491, 1391 cm$^{-1}$. Analytically calculated for $C_{17}H_{19}N_3O_2$: C, 68.67; H, 6.44; N, 14.13. Found: C, 68.78; H, 6.48; N, 14.11.

Example 19

This example illustrates a process for preparing 4-(2-methylphenyl)-6-(4-morpholinyl)-3-pyridinecarboxamide (Fig. I, Scheme I).

A mixture of 2-chloro-4-(2-methylphenyl)-6-(4-morpholinyl)-3-pyridine-carboxamide (5.00 g, 15.1 mmol), 2.31 mL (1.68 g, 16.5 mmol, 1.1 equiv) of triethylamine, 6.4 mg Pd(OH)$_2$ or 47 mg (0.0453 mmol, 0.30 mol %) of 20% palladium hydroxide on carbon [Pearlman's catalyst, 32.2% LOD], and 50 mL of methanol was stirred in a 300-mL Parr bottle at 25° C. and 40.2–31.2 psi hydrogen for 21 hours.

The pressure was vented and the mixture was filtered through a 2.0 g pad of Celite® on a coarse sintered glass funnel. The pad of Celite® was washed twice with 10 mL of methanol. Filtrate was concentrated and the resulting residue was taken up in 25 mL of toluene and 10 mL of $H_2O$. A solution of 660 mg (16.5 mmol) sodium hydroxide in 2 mL of $H_2O$ was added. The layers were separated and the aqueous layer was extracted three times with 10 mL toluene. The organic layers were combined, dried (MgSO$_4$), filtered, and concentrated to afford 4.24 g of 4-(2-methylphenyl)-6-(4-morpholinyl)-3-pyridinecarboxamide as a (94.6%) of colorless solid.

Example 20

This example illustrates a process for preparing 4-(2-methylphenyl)-6-(4-methylpiperazinyl)-3-pyridinecarboxamide (Fig. I, Scheme I).

A mixture of crude 5-cyano-4-(2-methylphenyl)-2-(4-methylpiperazinyl) pyridine (16.85 g, 57.6 mmol), 18 mL of toluene, and 27 mL (49.7 g, 507 mmol) of concentrated sulfuric acid was heated at 70° C. for 12 hours. The mixture was cooled and quenched with 200 mL of cold $H_2O$. Ethyl acetate was added followed by a solution of 45.6 g (1.14 mol) of sodium hydroxide in 200 mL of $H_2O$. Water (200 mL) was added and the layers were separated. The aqueous layer was extracted several times with 100 mL of ethyl. The organic layers were combined and concentrated to afford 17.55 g (98.1%) of 4-(2-methylphenyl)-6-(4-methylpiperazinyl)-3-pyridinecarboxamide as a colorless solid.

An analytical sample was prepared by recrystallization from isopropanol and final recrystallization from toluene-hexanes and revealed: m.p. 127.5–128.5° C.; $^1$H NMR (CDCl$_3$) δ 8.92 (s, 1H), 7.35 (m, J=1.5 Hz, J=7–8 Hz, 1H), 7.31–7.28 (m, 2H), 7.21 (m, 1H), 6.31 (s, 1H), 3.68 (br t, J=5 Hz, 4H), 2.51 (t, J=5 Hz, 4H), 2.35 (s, 3H), 2.15 (s, 3H); $^{13}$C NMR (CDCl$_3$) δ 168.4, 160.2, 152.1, 149.7, 139.4, 136.0, 130.9, 129.2, 128.4, 126.7, 117.3, 106.5, 55.0, 46.4, 44.8, 20.0; IR (KBr) 3459, 3324, 3273, 3168, 2967, 2935, 2849, 2795, 1665, 1581 cm$^{-1}$. Analytically calculated for $C_{18}H_{22}N_4O$: C, 69.65; H, 7.14; N, 18.05. Found: C, 69.76; H, 7.33; N, 17.92.

Example 21

This example illustrates a process for preparing 4-(4-fluoro-2-methylphenyl)-6-(1,1-dioxo-thiomorpholin-4-yl) pyridine-3-carboxamide (Fig. I, Scheme I).

A mixture of 5-cyano-4-(4-fluoro-2-methylphenyl)-2-(1,1-dioxo-thiomorpholin-4-yl)pyridine (14.80 g, 42.85 mmol), 15 mL of toluene, and 15 mL (27.6 g, 281 mmol) of concentrated sulfuric acid was heated in a 500-mL flask at 70° C. for 12 hours. The mixture was cooled and quenched with 150 mL cold $H_2O$. A solution of 22.8 g (570 mmol) of sodium hydroxide in 200 mL of $H_2O$ was added dropwise at 25–30° C. over 15 minutes. The precipitate was filtered, washed with $H_2O$, and dried to afford 15.68 g (100.7%) of 4-(4-fluoro-2-methylphenyl)-6-(1,1-dioxo-thiomorpholin-4-yl)pyridine-3-carboxamide as a colorless solid (2 wt % toluene remains).

An analytical sample was prepared by recrystallization from acetonitrile and revealed: m.p. 235–236° C.; $^1$H NMR (DMSO-d$_6$) δ 8.38 (s, 1H), 7.36 (br, 1H), 7.13 (dd, J=6 Hz, J=8.5 Hz, 1H), 7.09–7.07 (m, 2H), 7.02 (dt, J=2.5 Hz, J=8.5 Hz, 1H), 6.78 (s, 1H), 4.11 (br, 4H), 3.11 (br, 4H), 2.10 (s, 3H); $^{13}$C NMR (DMSO-d$_6$) δ 166.9, 160.3 (d, J=241 Hz), 155.8, 148.2, 146.3, 136.7 (d, J=8.0 Hz), 134.6 (d, J=2.8 Hz), 129.1 (d, J=8.4 Hz), 121.3, 114.8 (d, J=20.8 Hz), 110.8 (d, J=20.8 Hz), 107.2, 49.3, 42.1, 18.7; IR (KBr) 3446, 3324, 1372, 3147, 1663, 1608, 1575, 1496, 1399, 1121 cm$^{-1}$. Analytically calculated for $C_{17}H_{18}FN_3O_3S$: C, 56.19; H, 4.99; N, 11.56. Found: C, 56.14; H, 4.99; N, 11.88.

Example 22

This example illustrates a process for preparing 2,6-dichloro-4-(2-methylphenyl)-3-pyridinecarboxamide.

A mixture of 3-cyano-2,6-dichloro-4-(2-methylphenyl) pyridine (15.00 g, 57.0 mmol), and 15 mL of concentrated sulfuric acid was heated at 100° C. for 3 hours. The mixture was cooled and quenched with 150 mL of $H_2O$. The mixture was then extracted three times with ethyl acetate. The organic layers were combined, washed twice with 50 mL of $H_2O$, dried (MgSO$_4$), filtered, and concentrated to afford 11.99 g of near-colorless solid.

An analytical sample was prepared by recrystallization from toluene and revealed: m.p. 154–156° C.; $^1$H NMR (CDCl$_3$) δ 7.34 (dt, J=1.5 Hz, J=7.5 Hz, 1H), 7.27 (d, J=7.5 Hz, 1H), 7.23 (t, J=8 Hz, 1H), 7.20 (s, 1H), 7.12 (dd, J=1 Hz, J=7.5 Hz, 1H), 5.76 (br, 1H), 5.53 (br, 1H), 2.18 (s, 3H); $^{13}$C NMR (CDCl$_3$) δ 166.0, 153.4, 150.6, 147.4, 135.4, 135.3, 130.9, 129.7, 128.5, 126.1, 124.5, 95.0, 20.4; IR (KBr) 3391, 3303, 3167, 2360, 2350–2340, 1685, 1565, 1525 cm$^{-1}$.

Elemental analytically calculated for $C_{13}H_{10}Cl_2N_2O$: C, 55.54; H, 3.59; N, 9.96. Found: C, 55.51; H, 3.57; N, 9.81.

Example 23

This example illustrates a process for preparing 2-chloro-4-(2-methylphenyl)-6-(4-morpholinyl)-3-pyridinecarboxamide A mixture of 2-chloro-3-cyano-4-(2-methylphenyl)-6-(4-morpholinyl)pyridine (16.80 g, 53.5 mmol), 15 mL of toluene, and 14.3 mL (26.2 g, 268 mmol) of concentrated sulfuric acid was heated at 70° C. for 120 hours. The mixture was cooled and then quenched by addition of 160 mL of cold $H_2O$. Isopropyl acetate (150 mL) was added followed by a solution of 24.46 g (612 mmol) of sodium hydroxide in 120 mL of $H_2O$ at 20–25° C. The precipitate was filtered and dried to afford 16.83 g (94.8%) of colorless solid.

An analytical sample was prepared by recrystallization from toluene to afford shiny colorless needles and revealed: m.p. 217–219° C.; $^1$H NMR (CDCl$_3$) δ 7.28 (dd, 1H), 7.23 (d, J=7.0 Hz, 1H), 7.19 (dd, 1H), 7.12 (d, J=7.5 Hz, 1H), 6.32 (s, 1H), 5.72 (br, 1H), 5.43 (br, 1H), 3.79 (m, 4H), 3.55 (m, 4H), 2.20 (s, 3H); $^{13}$C NMR (CDCl$_3$) δ 167.9, 158.2, 152.4, 146.6, 138.0, 135.5, 130.6, 128.8, 128.5, 125.8, 120.8, 105.7, 66.7, 45.3, 20.3; IR (KBr) 3393, 3197, 2970, 2920, 2900, 2861, 1666, 1607, 1594, 1525 cm$^{-1}$. Elemental analytically calculated for $C_{17}H_{18}ClN_3O_2$: C, 61.54; H, 5.47; N, 12.66. Found: C, 61.65; H, 5.44; N, 12.56.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. A process for producing a carboxamide pyridine compound of the formula:

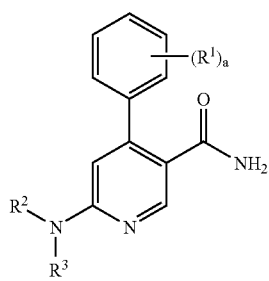

I said method comprising:
(a) reacting a pyridinium salt of the formula:

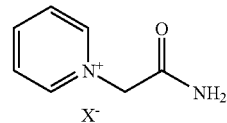

VI with an α-cyano-β-aryl acrylate compound of the formula:

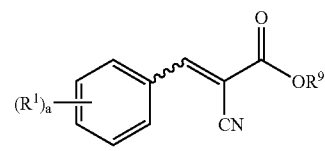

IV to produce a pyridinium zwitter ionic compound of the formula:

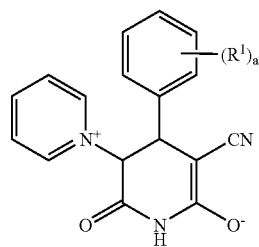

VII (b) reacting the pyridinium zwitter ionic compound with a reagent selected from the group consisting of POCl$_3$, PBr$_3$, and $(F_3CSO_2)_2O$, to form a cyanopyridine compound of formula:

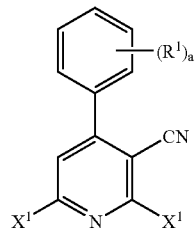

VIII (c) reacting the cyanopyridine compound of formula VIII with an amine compound of the formula HNR$^2$R$^3$ to form a tetra-substituted pyridine compound of the formula:

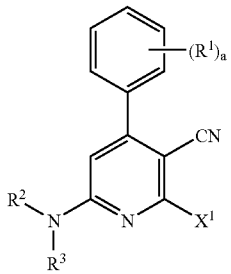

(d) hydrogenating the tetra-substituted pyridine compound formula IX in the presence of a hydrogenation catalyst to form a tri-substituted pyridine compound of the formula:

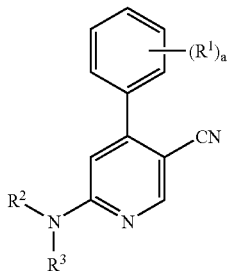

and (e) hydrolyzing the tri-substituted pyridine compound to form the carboxamide compound of Formula I, wherein each $R^1$ is independently lower alkyl, lower alkoxy, halogen, cyano or alkylamino;

a is an integer from 0 to 2;

$R^2$ is hydrogen, $C_{3-6}$ cycloalkyl, aralkyl, lower alkyl, hydroxylalkyl, —S(O)$_2$-lower alkyl, —S(O)$_2$—Ar$^1$, (optionally substituted N-heterocyclyl) alkyl, —C(=O)R$^3$, where Ar$^1$ is aryl;

$R^3$ is hydrogen, $C_{3-6}$ cycloalkyl, aralkyl or lower alkyl;

or $R^2$ and $R^3$ together with the nitrogen atom to which they are attached to form optionally substituted N-heterocyclyl;

or $R^2$ and $R^3$ together form =C(R$^5$)—R$^6$—NR$^7$R$^8$;

where $R^5$ is lower alkyl, or hydrogen;

$R^6$ is alkylene, or a bond; and each of $R^7$ and $R^8$ is independently hydrogen, $C_{3-6}$ cycloalkyl, aralkyl, or lower alkyl;

$R^9$ is lower alkyl;

$X^1$ is halide or trifluoromethanesufonate; and

X is halide.

2. The process according to claim 1, wherein the α-cyano-β-aryl acrylate compound of Formula IV is prepared by reacting a benzaldehyde compound of the formula:

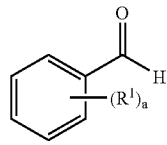

with an α-cyanoester compound of the formula:

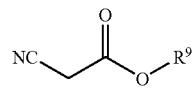

in the presence of a base, wherein $R^1$, a, and $R^9$ are those defined in claim 1.

3. The process according to claim 2, wherein the α-cyano-β-aryl acrylate compound of Formula IV is prepared in situ.

4. The process according to claim 2, wherein the base is morpholine.

5. The process according to claim 2, wherein said step of producing the α-cyanoester compound comprises conducting the reaction in an alcoholic solvent.

6. The process according to claim 5, wherein the alcoholic solvent comprises isopropanol, methanol, or a mixture thereof.

7. The process according to claim 2, wherein the reaction temperature of said α-cyanoester compound producing step is in the range of about 20° C. to about 33° C.

8. The process according to claim 1, wherein the reaction conditions for said step of producing the pyridinium zwitter ionic compound comprises a reaction solvent and the presence of an organic base.

9. The process according to claim 8, wherein the reaction solvent comprises ether, ketone, toluene, an alcohol, or a mixture thereof.

10. The process according to claim 9, wherein the alcohol is methanol.

11. The process according to claim 8, wherein the organic base is triethylamine.

12. The process according to claim 1, wherein $X^1$ is chloride.

13. The process according to claim 12, wherein the reagent for producing the cyano pyridine compound is phosphorous oxychloride.

14. The process according to claim 1, wherein the amine compound is selected from the group consisting of morpholine, 1-methylpiperazine, and thiomorpholine.

15. The process according to claim 14, wherein the amine compound is morpholine.

16. The process according to claim 1, wherein the hydrogenation catalyst is Pd(OH)$_2$.

17. The process according to claim 1, wherein said hydrolyzing step comprises contacting the tri-substituted pyridine compound with an acid.

18. The process according to claim 17, wherein the acid is selected from the group consisting of H$_2$SO$_4$, HCl, and acetic acid.

19. The process according to claim 18, wherein the acid is H$_2$SO$_4$.

20. The process according to claim 1, wherein each of $R^1$ is independently lower alkyl, alkoxy, halogen, cyano, or alkyamino.

21. The process according to claim 20, wherein R² and R³ together with the nitrogen atom to which they are attached to form optionally substituted N-heterocyclyl.

22. The process according to claim 21, wherein R² and R³ together with the nitrogen atom to which they are attached to form morpholin-4-yl, 4-methy-piperazine-1-yl or 1,1-dioxothiomorpholin-4-yl.

23. The process according to claim 1, wherein the carboxamide pyridine compound is:
  4-(2-methylphenyl)-6-(4-morpholinyl)-3-pyridinecarboxamide;
  4-(4-fluoro-2-methylphenyl)-6-(1,1-dioxo-thiomorpholin-4-yl)pyridine-3-carboxamide; or
  4-(2-methylphenyl)-6-(4-methylpiperazinyl)-3-pyridinecaboxamide.

24. A process for preparing an aminopyridine compound of the formula:

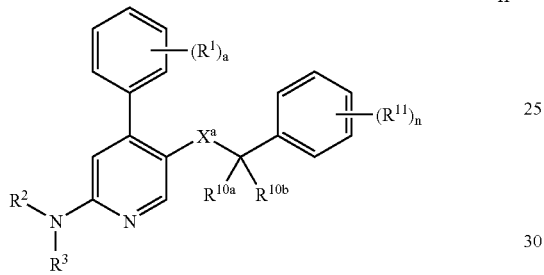

said process comprising:
  (a) reacting a pyridinium salt of the formula:

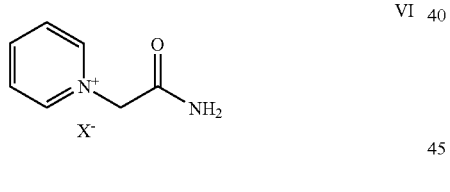

with an α-cyano-β-aryl acrylate compound of the formula:

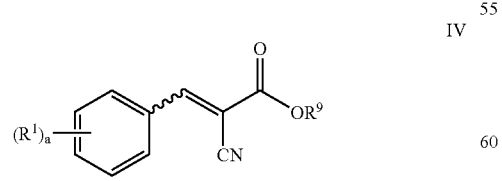

to produce a pyridinium zwitter ionic compound of the formula:

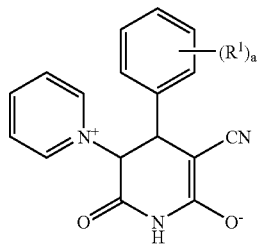

(b) reacting the pyridinium zwitter ionic compound with a reagent selected from the group consisting of POCl₃, PBr₃, and (F₃CSO₂)₂O, to form a cyanopyridine compound of formula:

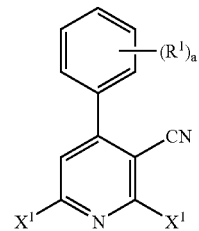

(c) reacting the cyanopyridine compound of formula VIII with an amine compound of the formula HNR²R³ to form a tetra-substituted pyridine compound of the formula:

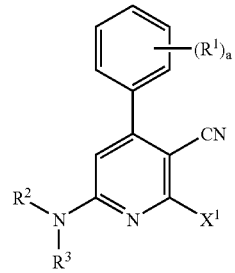

(d) hydrogenating the tetra-substituted pyridine compound of formula IX in the presence of a hydrogenation catalyst to form a tri-substituted pyridine compound of the formula:

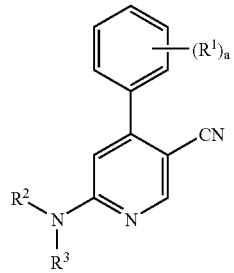

(e) hydrolyzing the tri-substituted pyridine compound to form the carboxamide pyridine compound of the formula:

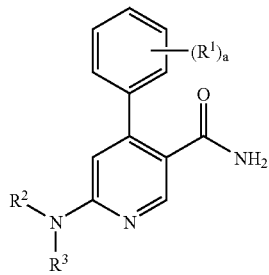

I (f) (i) (a) contacting the carboxamide pyridine compound of Formula I with an oxidizing agent in the presence of an alcohol of the formula $R^{13}$—OH to produce a carbamate pyridine compound of the formula:

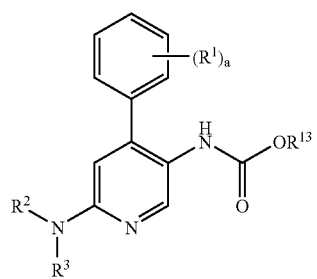

XII (b) reducing the carbamate pyridine compound of Formula XII with a reducing agent to produce a diaminopyridine compound of the formula:

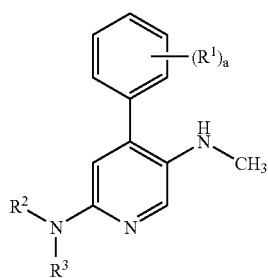

XIII (c) reacting the diaminopyridine compound of Formula XIII with a carbonyl compound of the formula:

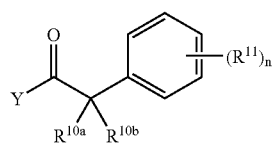

XIV to form the aminopyridine compound of Formula II, where $X^a$ is —N(CH$_3$)C(=O)—;

(d) optionally reacting the aminopyridine compound of Formula II, where $X^a$ is —N(CH$_3$)C(=O)—, with a second reducing agent to produce the aminopyridine compound of Formula II, where $X^a$ is —N(CH$_3$)—CH$_2$—; or (ii) (a) contacting the carboxamide pyridine compound of Formula I with a reducing agent to produce an alkylamino-substituted pyridine compound of the formula:

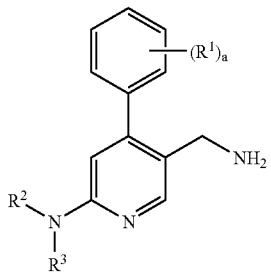

XV (b) reacting the alkylamino-substituted pyridine compound of Formula XIV with an aralkyl compound of the formula:

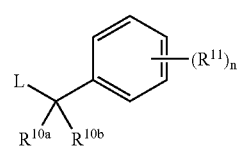

XVI to produce the aminopyridine compound of Formula II, where $X^a$ is —CH$_2$N(CH$_3$)—; or (iii) reacting the carboxamide pyridine compound of Formula I with an aralkyl compound of the formula:

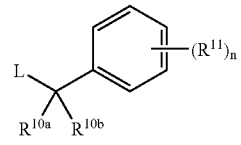

XVI in the presence of a base to produce the aminopyridine compound of Formula II, where $X^a$ is —C(=O)N(H)—, wherein
each $R^1$ is independently lower alkyl, lower alkoxy, halogen, cyano or alkylamino;
a is an integer from 0 to 2;
$R^2$ is hydrogen, $C_{3-6}$ cycloalkyl, aralkyl, lower alkyl, hydroxylalkyl, —S(O)$_2$-lower alkyl,
—S(O)$_2$—Ar$^1$, (optionally substituted N-heterocyclyl) alkyl, —C(=O)R$^3$, where Ar$^1$ is aryl;
$R^3$ is hydrogen, $C_{3-6}$ cycloalkyl, aralkyl or lower alkyl;
or $R^2$ and $R^3$ together with the nitrogen atom to which they are attached to form optionally substituted N-heterocyclyl;
or $R^2$ and $R^3$ together form =C(R$^5$)—R$^6$—NR$^7$R$^8$;
where
$R^5$ is lower alkyl, or hydrogen;
$R^6$ is alkylene, or a bond; and each of $R^7$ and $R^8$ is independently hydrogen, $C_{3-6}$ cycloalkyl, aralkyl, or lower alkyl;

$R^9$ is lower alkyl;

each of $R^{10a}$ and $R^{10b}$ is independently hydrogen or lower alkyl, or $R^{10a}$ and $R^{10b}$ together with the carbon atom to which they are attached to form a cycloalkyl group;

L is a leaving group;

each $R^{11}$ is independently halide, trifluoromethyl, lower alkoxy, or cyano, or two $R^{11}$ moieties form a moiety of the formula —$CR^w$=$CR^x$—$CR^y$=$CR^z$—, wherein each of $R^w$, $R^x$, $R^y$, and $R^z$ is independently hydrogen, lower alkyl or lower alkoxy, provided that at least two of $R^w$, $R^x$, $R^y$, and $R^z$ are hydrogen;

$R^{13}$ is lower alkyl;

n is an integer from 0 to 5;

Y is lower alkoxide or an acyl activating group;

$X^a$ is —C(=O)N($R^{14}$)—, —$R^{16}$—O—, —$R^{16}$—N($R^{14}$)—, —N($R^{14}$)C(=O)—, or —N($R^{14}$)—$R^{16}$—, where
  $R^{14}$ is hydrogen, $C_{3-6}$ cycloalkyl, aralkyl or lower alkyl; and
  $R^{16}$ is alkylene; and $X^1$ is halide or trifluoromethanesufonate; and X is halide.

25. The process according to claim 24, wherein the aminopyridine compound of Formula II is:

N-(3,5-bis-trifluoromethyl-benzyl)-N-methyl-6-[methyl-(2-morpholin-4-yl-ethyl)-amino]-4-o-tolyl-nicotinamide;

N-(3,5-bis-trifluoromethyl-benzyl)-N-methyl-6-morpholin-4yl-4-o-tolyl-nicotinamide;

N-(3,5-bis-trifluoromethyl-benzyl)-N-methyl-6-thiomorpholin-4-yl-4-o-tolyl-nicotinamide;

N-(3,5-bis-trifluoromethyl-benzyl)-N-methyl-6-(1-oxo-$1\lambda^6$-4-thiomorpholin-4-yl)-4-o-tolyl-nicotinamide;

N-(3,5-bis-trifluoromethyl-benzyl)-6-(1,1-dioxo-$1\lambda^6$-6-thiomorpholin-4-yl)-N-methyl-4-o-tolyl-nicotinamide;

N-(3,5-bis-trifluoromethyl-benzyl)-N-methyl-6-piperazin-1-yl-4-o-tolyl-nicotinamide;

N-(3,5-bis-trifluoromethyl-benzyl)-6-[4-(2-hydroxyethyl)-piperazin-1-yl)]-N-methyl-4-o-tolyl-nicotinamide;

2-(3,5-bis-trifluoromethyl-phenyl)-N-[6-(4-methyl-piperazin-1-yl)-4-o-tolyl-pyridin-3-yl]-N-methyl-isobutyramide;

2-(3,5-bis-trifluoromethyl-phenyl)-N-(6-morpholin-4-yl-4-o-tolyl-pyridin-3-yl)-N-methyl-isobutyramide;

2-(3,5-bis-trifluoromethyl-phenyl)-N-[4-(4-fluoro-2-methyl-phenyl)-6-(4-methyl-piperazin-1-yl)-pyridin-3-yl]-N-methyl-isobutyramide;

2-(3,5-bis-trifluoromethyl-phenyl)-N-[4-(2-chloro-phenyl)-pyridin-3-yl]-N-methyl-isobutyramide;

2-(3,5-bis-trifluoromethyl-phenyl)-N-methyl-N-(4-o-tolyl-pyridin-3-yl)-isobutyramide;

2-(3,5-bis-trifluoromethyl-phenyl)-N-methyl-N-[6-(4-pyridin-2-yl-piperazin-1-yl)-4-o-tolyl-pyridin-3-yl)-isobutyramide;

2-(3,5-bis-trifluoromethyl-phenyl)-N-(6-morpholin-4-yl-4-o-tolyl-pyridin-3-yl)-isobutyramide;

2-(3,5-bis-trifluoromethyl-phenyl)-N-[4-(2-chloro-phenyl)-6-dimethylamino-pyridin-3-yl]-isobutyramide;

2-(3,5-bis-trifluoromethyl-phenyl)-N-methyl-N-(6-piperazin-1-yl-4-o-tolyl-pyridin-3-yl)-isobutyramide; or 2-(3,5-bis-trifluoromethyl-phenyl)-N-[6-(1,1-dioxo-$1\lambda^6$-thiomorpholin-4-yl)-4-o -tolyl-pyridin-3-yl]-N-methyl-isobutyramide.

26. A process for preparing an amino-substituted cyanopyridine compound of the formula:

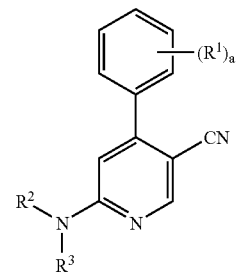

X said method comprising:

(a) reacting a pyridinium salt of the formula:

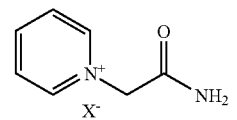

VI with an α-cyano-β-aryl acrylate compound of the formula:

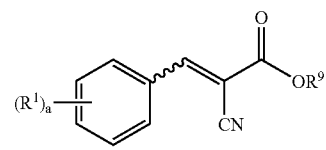

IV to produce a pyridinium zwitter ionic compound of the formula

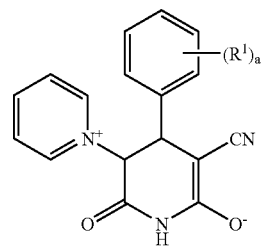

VII (b) reacting the pyridinium zwitter ionic compound with a reagent selected from the group consisting of POCl$_3$, PBr$_3$, and (F$_3$CSO$_2$)$_2$O, to form a cyanopyridine compound of formula:

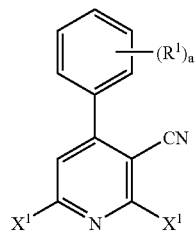

VIII (c) reacting the cyanopyridine compound of formula VIII with an amine compound of the formula $HNR^2R^3$ to form a tetra-substituted pyridine compound of the formula:

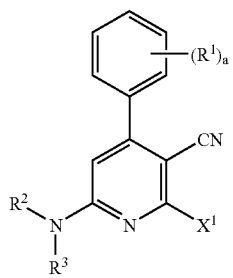

IX and (d) hydrogenating the tetra-substituted pyridine compound formula IX in the presence of a hydrogenation catalyst to form the amino-substituted cyanopyridine compound, wherein each $R^1$ is independently lower alkyl, lower alkoxy, halogen, cyano or alkylamino;

a is an integer from 0 to 2;

$R^2$ is hydrogen, $C_{3-6}$ cycloalkyl, aralkyl, lower alkyl, hydroxylalkyl, —$S(O)_2$-lower alkyl, —$S(O)_2$—$Ar^1$, (optionally substituted N-heterocyclyl) alkyl, —$C(=O)R^3$, where $Ar^1$ is aryl;

$R^3$ is hydrogen, $C_{3-6}$ cycloalkyl, aralkyl or lower alkyl;

or $R^2$ and $R^3$ together with the nitrogen atom to which they are attached to form optionally substituted N-heterocyclyl;

or $R^2$ and $R^3$ together form =$C(R^5)$—$R^6$—$NR^7R^8$;

where $R^5$ is lower alkyl, or hydrogen;

$R^6$ is alkylene, or a bond; and each of $R^7$ and $R^8$ is independently hydrogen, $C_{3-6}$ cycloalkyl, aralkyl, or lower alkyl;

$R^9$ is lower alkyl;

X is halide; and $X^1$ is halide or trifluoromethanesufonate.

27. The process according to claim 26, wherein the α-cyano-β-aryl acrylate compound of Formula IV is prepared by reacting a benzaldehyde compound of the formula:

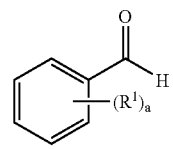

III with an α-cyanoester compound of the formula:

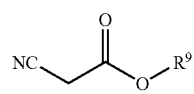

XI in the presence of a base.

28. The process according to claim 26, wherein the α-cyano-β-aryl acrylate compound of Formula IV is prepared in situ.

29. The process according to claim 26, wherein the base is morpholine.

30. The process according to claim 26, wherein said step of producing the α-cyanoester compound comprises conducting the reaction in an alcoholic solvent.

31. The process according to claim 30, wherein the alcoholic solvent comprises isopropanol, methanol, or a mixture thereof.

32. The process according to claim 26, wherein the amino-substituted cyanopyridine compound is:

5-cyano-4-(2-methylphenyl)-2-(4-morpholinyl)pyridine; or 5-cyano-4-(2-methylphenyl)-2-(4-methylpiperazinyl)pyridine.

* * * * *